United States Patent
Olson et al.

(10) Patent No.: US 7,071,318 B2
(45) Date of Patent: Jul. 4, 2006

(54) METHODS AND COMPOSITIONS FOR STABILIZING MICROTUBULES AND INTERMEDIATE FILAMENTS IN STRIATED MUSCLE CELLS

(75) Inventors: Eric N. Olson, Dallas, TX (US); Jeffrey A. Spencer, Grand Prairie, TX (US)

(73) Assignee: Board of Regents, The University of Texas System, Austin, TX (US)

(*) Notice: Subject to any disclaimer, the term of this patent is extended or adjusted under 35 U.S.C. 154(b) by 236 days.

(21) Appl. No.: 10/775,649

(22) Filed: Feb. 10, 2004

(65) Prior Publication Data

US 2004/0132160 A1  Jul. 8, 2004

Related U.S. Application Data

(62) Division of application No. 09/908,988, filed on Jul. 18, 2001, now Pat. No. 6,740,751.

(60) Provisional application No. 60/219,020, filed on Jul. 18, 2000.

(51) Int. Cl.
C12N 15/12 (2006.01)
C12N 15/74 (2006.01)
C12N 15/79 (2006.01)
C07K 14/435 (2006.01)

(52) U.S. Cl. ............... 536/23.5; 435/69.1; 435/252.3; 435/320.1; 530/350

(58) Field of Classification Search ............... 536/23.5; 435/69.1, 252.3, 320.1; 530/350
See application file for complete search history.

(56) References Cited

U.S. PATENT DOCUMENTS

| 5,403,711 A | 4/1995 | Walder et al. ............... 435/6 |
| 6,060,240 A | 5/2000 | Kamb et al. ............... 435/6 |
| 6,096,720 A | 8/2000 | Love et al. ............... 514/44 |
| 6,248,724 B1 | 6/2001 | Moore et al. ............... 514/44 |
| 2003/0166887 A1* | 9/2003 | Yates et al. ............... 536/23.1 |
| 2004/0018513 A1* | 1/2004 | Downing et al. ............... 435/6 |

FOREIGN PATENT DOCUMENTS

| WO | WO 00/58473 | 10/2000 |
| WO | WO 01/42302 | 6/2001 |
| WO | WO 01/55322 | 8/2001 |
| WO | WO 01/62767 | 8/2001 |

OTHER PUBLICATIONS

Antin et al., "Taxol induces postmitotic myoblasts to assemble interdigitating microtubule-myosin arrays that exclude actin filaments," *J. Cell Biol.*, 90(2):300-308, 1981.
Bartkiewicz et al., "Leucine zipper-mediated homodimerization of the adaptor protein c-Cbl. A role in c-Cbl's tyrosine phosphorylation and its association with epidermal growht factor receptor," *J. Biol. Chem.*, 274(43):30887-30895, 1999.

(Continued)

*Primary Examiner*—Nashaat T. Nashed
*Assistant Examiner*—William W. Moore
(74) *Attorney, Agent, or Firm*—Fulbright & Jaworski

(57) ABSTRACT

The present invention discloses new muscle ring finger (MURF) proteins designate MURF-1, MURF-2 and MURF-3. The genes encoding these MURFs also are provided. MURFs interact with microtubules and thus play a role in cytoskeletal function, mitosis and cell growth. Thus, the uses of MURFs in diagnosis, treatment and drug screening, in particular relation to cardiomyopathies, are described.

15 Claims, 10 Drawing Sheets

OTHER PUBLICATIONS

Benjamin et al., "Temporospatial expression of the small HSP/alpha B-crystallin in cardiac and skeletal muscle during mouse development," *Dev. Dyn.*, 208(1):75-84, 1997.

Borden, "RING fingers and B-boxes: zinc-binding protein-proten interaction domains," *Biochem. Cell Biol.*, 76:351-358, 1998.

Buchner et al., "MID2, a homologue of the Opitz syndrome gene MID 1: similarities in subcellular localization and differences in expression during development," *Hum.Mol. Genet.*, 8:1397-1407, 1999.

Cainarca et al., "Functional characterization of the Opitz syndrome gene product (midin): evidence for homodimerization and association with microtubules throughout the cell cycle," *Hum. Mol. Genet.*, 8:1387-1396, 1999.

Cao et al., "Involvement of the rfp tripartite motif in protein-protein interactions and subcellular distribution," *J. Cell Sci.*, 110(Pt 14):1563-1571, 1997.

De The et al., "The PML-RARα fusion mRNA generated by the t(15;17) translocation in acute promyelocytic leukemia encodes a functionally altered RAR," *Cell*, 66(4):675-684, 1991.

Francis et al., "Doublecortin is a developmentally regulated, microtubule-associated protein expressed in migrating and differentiating neurons," *Neuron.*, 23:247-256, 1999.

Freemont, "Ubiquitination: RING for destruction?" *Curr Biol.*, 10(2):R84-87, 2000.

Gleeson et al., "Doublecortin is a microtubule-associated protein, and is expressed widely by migrating neurons," *Neuron.*, 2:257-271, 1999.

Gunderson et al., "Generation of stable, posttranslationally modified microtubule array is an early event in myogenic differentiation," *J. Cell Biol.*, 109:2275-2288, 1989.

Hsieh et al., "The RING finger/B-Box factor TAM-1 and a retinoblastoma-like protein LIN-35 modualte context-dependent gene silencing in Caenorhabditis elegans," *Genes Dev.*, 13(22):2958-2970, 1999.

Kaech et al., "Cytoskeletal plasticity in cells expressing neuronal microtubule-associated proteins," *Neuron*, 17(6):1189-1199, 1996.

Kaufman et al., "The M-cadherin catenin complex interacts with microtubules in skeletal muscle cells: implications for the fusion of myoblasts," *J. Cell Sci.*, 112:55-67, 1999.

Kosik, "Tau protein and neurodegenration," *Mol. Neurobiol.*, 4(3-4):171-179, 1990.

Li et al., "The association of Xenopus nuclear factor 7 with subcellular structures is dependent upon phosphorylation and specific domains," *Exp. Cell Res.*, 13(2):473-481, 1994.

Lo Nigro et al., "Point mutations and an intragenic deletion in LISI, the lissencephaly causative gene in isolated lissencephaly sequence and Miller-Dieker syndrome," *Hum. Mol. Genet.*, 6(2):157-164, 1997.

Mangan and Olmsted, "A muscle-specific variant of the microtubule-associated protein 4 (MAP4) is required for myogenesis," *Dev.*, 122:771-781, 1996.

Marszalek et al., "Situs inversus and embryonic ciliary morphogenesis defects in mouse mutants lacking the KIF3A subunit of kinesin-II," *Proc. Nat'l Acad. Sci.*, 96(9):5043-5048, 1999.

Nguyen et al., "Overexpression of full- or partial-length MAP4 stabilizes microtubules and alters cell growth," *J. Cell Sci.*, 110 ( Pt 2):281-294, 1997.

Nguyen et al., "Stabilization and functional modulation of microtubules by microtubule-associated protein 4," *Biol. Bull.*, 194(3):354-357, 1998.

Quaderi et al., "Opitz G/BBB syndrome, a defect in midline development, is due to mutation in a new RING finger gene on Xp22," *Nat. Gen.*, 17:285-291, 1997

Rawls et al., "Overlapping functions of the myogenic bHLH genes MRF4 and MyoD revealed in double mutant mice," *Development*, 125(13):2349-2358, 1998.

Sapir et al., "LIS1 is a microtubule-associated phosphoprotein," *Eur. J. Biochem.*, 265(1):181-188, 1999.

Sapir et al., "Reduction of microtubule castastrophe events by LIS1, platelet-activating factor acetylhydrolase subunit," *EMBO J.*, 16(23):6977-6984, 1997.

Sato et al., "Microtubule stabilization in pressure overload cardiac hypertrophy," *J. Cell Biol.*, 139:963-973, 1997.

Saurin et al., "Does this have a familiar RING?" *TIBS*, 21(6):208-214, 1996.

Schulze et al., "Posttranslational modification and microtubule stability," *J. Cell Biol.*, 105: 2167-2177, 1987.

Schweiger et al., "The Opitz syndrome gene product, MID1, associates with microtubules," *Proc. Nat'l Acad. Sci. USA*, 96:2794-2799, 1999.

Sotiropoulos et al., "Signal-regulated activation of serum response factor is mediated by changes in actin dynamics," *Cell.*, 98: 159-169, 1999.

Spencer and Misra, "Expression of the serum response factor gene is regulated by serum response factor binding sites," *J. Biol. Chem.*, 271(28):16535-16543, 1996.

Spencer et al., "Cooperative transcriptional activation by serum response factor and the high mobility group protein SSRP1," *J. Biol. Chem.*, 274(22):15686-15693, 1999.

Stone and Chambers, "Microtubule inhibitors elicit differential effects on MAP kinase (JNK, ERK, and p38) signaling pathways in human KB-3 carcinoma cells," *Exp. Cell. Res.*, 254: 110-119, 2000.

Supp et al., "Targeted delection of the ATP binding domain of left-right dynein confirms its role in specifying development of left-right asymmetries," *Dev.*, 126:5495-5504, 1999.

Takeda et al., "Left-right asymmetry and kinesin superfamily protein KIF3A: new insights in determination of laterality and mesoderm induction by kif3A '/' mice analysis," *J. Cell Biol.*, 145:825-836, 1999.

Takemura et al., "Increased microtubule stability and alpha tubulin acetylation in cells transfected with microtubule-associated proteins MAP1B, MAP2 or tau," *J. Cell Sci.*, 103 ( Pt 4):953-964, 1992.

Tolnay and Probst, "Review: tau protein pathology in Alzheimer's disease and related disorders," *Neuropathol. Appl. Neurobiol.*, 25(3):171-187, 1999.

Toyama et al., "Effects of taxol and Colcemid on myofibrillogenesis," *Proc. Natl. Acad. Sci.*, 79(21):6556-6560, 1982.

Wang et al., "Removal of MAP4 from microtubules in vivo produces no observable phenotype at the cellular level," *J. Cell Biol.*, 132(3):345-357, 1996.

Webster, "Neonatal rat cardiomyocytes possess a large population of stable microtubules that is enriched in post-translationally modified subunits," *J. Mol. Cell Cardio.*, 29:2813-2824, 1997.

Zestser et al., "p38 mitrogen-activated protein kinase pathway promotes skeletal muscle differentiation. Participation of the MEF2C transcription factor," *J. Biol. Chem.*, 274: 5193-5200, 1999.

Centner et al., "Identification of muscle specific ring finger proteins as potential regulators of the titin kinase domain," *J. Mol. Biol.*, 306:717-726, 2001.
Database EMBL accession No. AA840584.
Database EMBL accession No. AAS25842.
Database EMBL accession No. AAS25855.
Database EMBL accession No. AAU15855.
Database EMBL accession No. AAU15868.
Database EMBL accession No. AB030912.
Database EMBL accession No. AF294790.
Database EMBL accession No. AI644642.
Database EMBL accession No. AJ291712.
Database EMBL accession No. AJ291713.
Database EMBL accession No. AV006036.
Database EMBL accession No. AV006120.
Lee et al., "Myosin light chain-2 luciferase transgenic mice reveal distinct regulatory programs for cardiac skeletal muscle-specific expression of a single contractile protein gene," *J. Biol. Chem.*, 267(22):15875-15885, 1992.
Spencer et al., "Regulation of microtubule dynamics and myogenic differentiation by MURF, a striated muscle RING-finger protein," *J. Cell Biol.*, 150(4):771-784, 2000.
Lee et al., EMBL database, Accession No. AA800245, published Apr. 30, 1998.
Konno et al., EMBL database, Accession No. BB140247, published Jun. 28, 2000.

* cited by examiner

FIG. 10

METHODS AND COMPOSITIONS FOR STABILIZING MICROTUBULES AND INTERMEDIATE FILAMENTS IN STRIATED MUSCLE CELLS

The present application claims priority to U.S. Provisional Application Ser. No. 60/219,020, filed Jul. 18, 2000, and is a division of U.S. patent application Ser. No. 09/908,988 filed on Jul. 18, 2001 now U.S. Pat. No. 6,740,751. Additionally, all patents, published patent applications, and other references cited throughout this specification are hereby incorporated by reference in their entireties.

The government may own rights in the present invention pursuant to grant number HL07360 from the National Institutes of Health.

BACKGROUND OF THE INVENTION

1. Field of the Invention

The present invention relates generally to the fields of developmental biology and molecular biology. More particularly, it concerns a striated muscle RING finger protein (MURF) involved in microtubule and intermediate filament stabilization of striated muscle cells.

2. Description of Related Art

The RING-finger is an unusual type of Cys-His zinc-binding motif found in a growing number of proteins with roles in signal transduction, gene transcription, differentiation, and morphogenesis (Borden, 1998; Saurin et al., 1996). A RING-B-box-coiled-coil (RBCC) subclass of RING-finger proteins contains an N-terminal RING-finger followed by a single or multiple additional zinc-finger domains, termed B-boxes, and a leucine-rich coiled-coil domain (Borden, 1998). The tripartite organization of these domains is evolutionarily conserved, suggesting an integrated and functional role for this overall protein structure. It should also be noted that the RING-finger and B-box motifs have been identified based on sequence homologies and are predicted to function as zinc-binding domains. However, their precise functions have not been fully elucidated. There is evidence suggesting that the RING-finger, B-box and coiled-coil domains mediate protein-protein interactions.

Several RBCC proteins have been implicated in oncogenesis. The RBCC member PML becomes fused to the retinoic acid receptor alpha in acute promyelocytic leukemia (De The et al., 1991). Similarly, the RBCC proteins BRCA1, Cb1, Rfp, TIF1, and MDM2 have been demonstrated to be oncogenic when fused to other factors through chromosomal translocation events (Saurin et al., 1996). Other RBCC proteins have been implicated in signal transduction, organellar biogenesis, chromosomal dynamics, viral pathogenesis, transcription, and developmental patterning (Saurin et al., 1996).

Recently, a complex congenital human disease, Opitz G/BBB syndrome, was shown to result from mutations in the RBCC protein, Mid1 (Quaderi et al., 1997). Opitz G/BBB syndrome is characterized by abnormalities of midline structures, including hypertelorism, clefts of lip and palate, larygotracheoesophageal defects, hypospadias, imperforate anus, and developmental delay. The Mid1 gene product is widely expressed during development and interacts with microtubules throughout the cell cycle (Cainarca et al., 1999). Overexpression of Mid1 leads to a stable population of microtubules resistant to depolymerization (Schweiger et al., 1999). Interestingly, mutations of Mid1 that are linked to Opitz G/BBB syndrome severely diminish the ability of Mid1 to interact with microtubules, suggesting that Mid1-microtubule interaction and/or microtubule dynamics are involved in the processes required for normal development of the midline structures affected in Opitz G/BBB syndrome.

Many questions remain regarding the function of Mid1-type proteins and their interactions with microtbules. Nonetheless, it is clear that such molecules play an important role in development, function and pathology of a wide variety of cell types.

SUMMARY OF THE INVENTION

Therefore, in one aspect of the invention, there is provide a DNA segment encoding a MURF-1, MURF-2 or MURF-3 polypeptide. The MURF-1, MURF-2 or MURF-3 polypeptide may be human, mouse, dog, rabbit, rat, *Drosphila,* yeast or other species. In a particular embodiment, the MURF-1 polypeptide has the sequence of SEQ ID NO:2, the MURF-2 polypeptide has the sequence of SEQ ID NO:4, and the MURF-3 polypeptide has the sequence of SEQ ID NO:6. In yet more particular embodiments, the MURF-1 DNA segment has the sequence of SEQ ID NO:1, the MURF-2 DNA segment has the sequence of SEQ ID NO:3, and the MURF-3 DNA segment has the sequence of SEQ ID NO:5.

The DNA segment may be positioned under the control of a promoter, for example, a promoter not native to the MURF-1, MURF-2 or MURF-3 coding region. The MURF-1, MURF-2 or MURF-3 coding region gene may be positioned in reverse orientation to the promoter, thereby capable of expressing an antisense product. The DNA segment may further comprise a polyadenylation signal. The DNA segment may further comprise an origin of replication. The DNA segment may be viral vector or a non-viral vector.

In another aspect of the invention, there is provided a host cell comprising a DNA segment that encodes a MURF-1, MURF-2 or MURF-3 polypeptide, wherein said DNA segment comprises a promoter heterologous to the MURF-1, MURF-2 or MURF-3 coding region. The host cell may further be defined as a prokaryotic host cell or a eukaryotic host cell. The host cell may be a secretory cell.

In yet another aspect of the invention, there is provided a method of using a host cell comprising an expression cassette comprising a polynucleotide encoding a MURF-1, MURF-2 or MURF-3 polypeptide and a promoter active in said host cell, said promoter directing the expression of said polypeptide, said method comprising culturing the host cell under conditions suitable for the expression of the MURF-1, MURF-2 or MURF-3 polypeptide.

In still yet another aspect of the invention, there is provided an isolated nucleic acid segment comprising at least 15 contiguous nucleotides of SEQ ID NO:1, SEQ ID NO:3 or SEQ ID NO:5. The isolated nucleic acid segment may be 15, 20, 25, 30, 35, 40, 45, 50, 75 or 100 nucleotides in length. The number of contiguous nucleotides may be increased to 20, 25, 30, 35, 40, 45, 50, 75 or 100.

In still yet an additional embodiment, there is provided as an isolated nucleic acid segment of from 14 to about 888 nucleotides in length that hybridizes to the nucleic acid segment of SEQ ID NO:1, SEQ ID NO:3 SEQ ID NO:5, or complements thereof, under standard hybridization conditions. The isolated nucleic acid segment may further comprise an origin of replication. The isolated nucleic acid may be a viral vector selected from the group consisting of retrovirus, adenovirus, herpesvirus, vaccinia virus, poxvirus, and adeno-associated virus. Further, the isolated nucleic acid may be packaged in a liposome.

In another aspect of the invention, there is provided a nucleic acid detection kit comprising, in suitable container means, an isolated nucleic acid segment that hybridizes under high stringency conditions to the nucleic acid sequence of SEQ ID NO:1, SEQ ID NO:3 or SEQ ID NO:5, or complements thereof. The may further comprise a detection reagent, for example, a detectable label that is linked to said nucleic acid segment.

In yet another embodiment, there is provided a composition comprising a purified MURF-1, MURF-2 or MURF-3 protein or peptide that includes a contiguous amino acid sequence from SEQ ID NO:2, SEQ ID NO:4 or SEQ ID NO:6. In still yet another embodiment, there is provided a purified MURF protein having the amino acid sequence of SEQ ID NO:2, SEQ ID NO:4 or SEQ ID NO:6. In still a further embodiment, there is provided a recombinant MURF-1, MURF-2 or MURF-3 protein or peptide prepared by expressing a DNA segment that encodes a MURF-1, MURF-2 or MURF-3 protein or peptide in a recombinant host cell and purifying the expressed MURF-1, MURF-2 or MURF-3 protein or peptide away from total recombinant host cell components.

In another embodiment, there is provided an isolated peptide of between about 10 and about 50 amino acids in length, comprising a contiguous amino acid sequence from the sequence of SEQ ID NO:2, SEQ ID NO:4 or SEQ ID NO:6. The peptide may be about 10, 15, 20, 25, 30, 35, 40, 45, 50, 75 or 100 amino acids in length. In yet another embodiment, there is provided an antibody composition that binds to a protein or peptide that includes an epitope from SEQ ID NO:2, SEQ ID NO:4 or SEQ ID NO:6. The antibody composition may comprise monoclonal antibodies or polyclonal antibodies. The antibodies of the composition are operatively attached to a detectable label, the label could be selected from the group consisting of a fluorescent label, a chemiluminescent label, a electroluminescent label, a radiolabel and an enzyme. Also provided is a hybridoma cell that produces a monoclonal antibody that binds immunologically to MURF-1, MURF-2 or MURF-3. Also provided is an immunodetection kit comprising, in suitable container means, a first antibody that binds to a MURF-1, MURF-2 or MURF-3 protein or peptide.

In still yet another embodiment, there is provided a method for detecting alterations in MURF-1, MURF-2 or MURF-3 function in a cell comprising assessing the structure or expression level of a MURF-1, MURF-2 or MURF-3 polypeptide. The method may comprise determining the structure of a MURF-1, MURF-2 or MURF-3 gene, for example, sequencing a MURF-1, MURF-2 or MURF-3 gene, or Southern or Northern analysis of a MURF-1, MURF-2 or MURF-3 transcript or gene. Alternatively, the assessing may comprise determining the level of a MURF-1, MURF-2 or MURF-3 protein or transcript in the cell, for example, by Northern analysis of MURF-1, MURF-2 or MURF-3 transcripts, or immunodetection of MURF-1, MURF-2 or MURF-3 protein levels (ELISA, Western blot).

In yet a further embodiment, there is provided a method for increasing MURF-1, MURF-2 or MURF-3 activity in cell comprising administering to the cell with an expression construct comprising a MURF-1, MURF-2 or MURF-3 coding region under the control of a promoter active in the cell.

In still yet a further embodiment, there is provided a method of screening a candidate substance for MURF-1, MURF-2 or MURF-3 binding activity comprising (i) providing a MURF-1, MURF-2 or MURF-3 polypeptide; (ii) contacting the MURF-1, MURF-2 or MURF-3 polypeptide with the candidate substance; and (iii) determining the binding of the candidate substance to the MURF-1, MURF-2 or MURF-3 polypeptide. The assay may be performed in a cell free system or in a cell.

In another embodiment, there is provided a method of screening a candidate substance for an effect on MURF-1, MURF-2 or MURF-3 levels in a cell comprising (i) providing a cell that expresses MURF-1, MURF-2 or MURF-3 polypeptide; (ii) contacting the cell with the candidate substance; and (iii) determining the effect of the candidate substance on MURF-1, MURF-2 or MURF-3 polypeptide level.

In still another embodiment, there is provided a method of screening a candidate substance for an effect on MURF-1, MURF-2 or MURF-3 expression in a cell comprising (i) providing a cell that expresses MURF-1, MURF-2 or MURF-3 polypeptide; (ii) contacting the cell with the candidate substance; and (iii) determining the effect of the candidate substance on MURF-1, MURF-2 or MURF-3 mRNA levels.

In still yet another embodiment, there is provided a method of screening a candidate substance for an effect on MURF-1, MURF-2 or MURF-3 interaction with microtubules comprising (i) providing a microtubule composition; (ii) contacting the microtubule composition with MURF-1, MURF-2 or MURF-3 polypeptide in the presence of the candidate substance; and (iii) assessing the interaction of MURF-1, MURF-2 or MURF-3 with the microtubule composition in the presence of the candidate substance, wherein a change in the interaction of MURF-1, MURF-2 or MURF-3 with the microtubule composition, as compared to the interaction in the absence of the candidate substance, indicates that the candidate substance modulates the interaction of MURF-1, MURF-2 or MURF-3 and microtubules. Step (iii) may comprise a cosedimentation assay.

In another embodiment, there is provided a method for screening a candidate substance for an effect on MURF-1, MURF-2 or MURF-3 homodimeraization comprising (i) providing a MURF-1, MURF-2 or MURF-3 polypeptide composition; (ii) contacting the composition with the candidate substance; and (iii) determining the effect of the candidate substance on MURF-1, MURF-2 or MURF-3 homodimerization.

In still another embodiment, there is provided a method of screening a candidate substance for an effect on MURF-1, MURF-2 or MURF-3 directed glutamic acid modification of microtubules comprising (i) providing a cell that expresses MURF-1, MURF-2 or MURF-3 polypeptide; (ii) contacting the cell with the candidate substance; and (iii) determining the effect of the candidate substance on glutamic acid modification of microtubules.

In yet a further embodiment, there is provided a method of screening a candidate substance for an effect on MURF-1, MURF-2 or MURF-3 stabilization of microtubules comprising (i) providing a microtubule composition; (ii) contacting the microtubule composition with MURF-1, MURF-2 or MURF-3 polypeptide in the presence of the candidate substance; and (iii) assessing the stability of the microtubule composition in the presence of the candidate substance, wherein a change in the stability of MURF-1, MURF-2 or MURF-3 with the microtubule composition, as compared to the stability in the absence of the candidate substance, indicates that the candidate substance modulates the stability microtubules.

Also provided is a transgenic non-human mammal, cells of which comprise a MURF-1, MURF-2 or MURF-3 encoding nucleic acid segment integrated into their genome, wherein the MURF-1, MURF-2 or MURF-3 encoding nucleic acid is under the control of a heterologous promoter. The promoter may be a tissue specific promoter, for example, a muscle specific promoter, such as myosin light chain-2 promoter, alpha actin promoter, troponin 1 promoter, $Na^+/Ca^{2+}$ exchanger promoter, dystrophin promoter, creatine kinase promoter, alpha7 integrin promoter, brain natriuretic peptide promoter, and alpha B-crystallin/small heat shock protein promoter. The transgenic mammal may be a mouse.

In another embodiment, there is provided a method of treating cardiac failure comprising increasing MURF-1, MURF-2 or MURF-3 activity in a cardiac cell, wherein said increased MURF-1, MURF-2 or MURF-3 activity stabilizes microtubules and/or intermediate filaments. The method may comprise increasing MURF-1, MURF-2 or MURF-3 activity by contacting said cardiac cell with an expression cassette that comprises a polynucleotide encoding a MURF-1, MURF-2 or MURF-3 polypeptide and a promoter active in said cardiac cell, wherein said promoter directing the expression of said polypeptide. The promoter may be a cardiac specific promoter. The contacting may be by intravenous or intraarterial administration of a vector comprising said expression cassette.

In yet a further embodiment, there is provided a method of decreasing MURF-1, MURF-2 or MURF-3 activity in a cell comprising administering to said cell an agent that inhibits MURF-1, MURF-2 and/or MURF-3 activity. The agent be a small molecule, an antisense molecule that hybridizes to MURF-1, MURF-2 and/or MURF-3 transcripts, a ribozyme molecule that cleaves MURF-1, MURF-2 and/or MURF-3 transcripts. Also provided is a method of blocking MURF-1, MURF-2 or MURF-3 expression in a cell comprising administering to said cell an agent that inhibits transcription or translation of MURF-1, MURF-2 and/or MURF-3.

In still a further embodiment, there is provided a method of screening a candidate sustance for an effect on MURF-1, MURF-2 or MURF-3 interaction with intermediate filaments comprising (i) providing an intermediate filament composition; (ii) contacting the intermediate filament composition with MURF-1, MURF-2 or MURF-3 polypeptide in the presence of the candidate substance; and (iii) assessing the interaction of MURF-1, MURF-2 or MURF-3 with the intermediate filament composition in the presence of the candidate substance, wherein a change in the interaction of MURF-1, MURF-2 or MURF-3 with the intermediate filament composition, as compared to the interaction in the absence of the candidate substance, indicates that the candidate substance modulates the interaction of MURF-1, MURF-2 or MURF-3 and intermediate filament. The method may be in a cell or a cell free system. It may be performed in vivo. The method may comprise a cosedimentation assay. The intermediate filaments may be one or more of desmin, vimentin and cytokeratin.

In yet still a further embodiment, there is provided a method for screening a candidate substance for an effect on MURF heterodimerization comprising (i) providing two or more of a MURF-1, MURF-2 or MURF-3 polypeptide composition; (ii) contacting the compositions with the candidate substance; and (iii) determining the effect of the candidate substance on the heterodimerization of two or more of MURF-1, MURF-2 or MURF-3.

In each of the preceding screening embodiments, there also is provided similar methods for the production of a modulator, comprising each of the aforementioned screening steps, followed by the additional step of producing the modulator so identified.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A Deduced amino acid sequence of MURF-1. The RING-finger domain is boxed, the B-box domain is shaded, and the coiled-coil domain is underlined. FIG. 1B. Schematic diagrams of MURF-1 and Midline proteins. FIGS. 1C and 1D. Amino acid homologies between the RING-finger and B-box domains, respectively, of MURF-1 and Midline proteins.

FIG. 2A. Detection of MURF-1 transcripts by in situ hybridization to mouse embryo sections. A transverse section through an E8.5 embryo shows expression exclusively in the cardiac forming region. A transverse section through an E10.5 embryo shows expression in the heart and myotomes. A sagittal section through an E16.5 embryo shows expression throughout skeletal muscle and heart: a, atria; m, myotome; hf, head folds; nt, neural tube; v, ventricle. FIG. 2B. Northern analysis of polyA+ mRNA from adult mouse tissues. A 1.5 kb MURF-1 transcript is detected only in heart and skeletal muscle. FIG. 2C. Western blot analysis of MURF-1 protein in extracts from adult mouse tissues. The 41 kD MURF-1 protein is detected only in heart and skeletal muscle. Blotting with anti-tubulin antibody confirmed equal quantities of protein in each lane. FIG. 1D. RT-PCR analysis of RNA from C2 cells in growth medium (GM) or differentiation medium (DM) for 1 or 3 days, as indicated. MURF-1 transcripts are detected at low levels in undifferentiated myoblasts in GM and are upregulated during differentiation. L7 is expressed constitutively and is a control for RNA loading.

FIG. 3A. Microtubule cosedimentation of endogenous MURF-1 protein from striated muscle. Microtubules from soluble extracts from striated muscle were induced to polymerize as described in Material and Methods. MURF-1 is contained in the microtubule pellet from striated muscle. FIG. 3B. Localization of MURF-1 to microtubules of C2 myotubes detected by immunofluorescence with anti-MURF-1 antibody, as described in Materials and Methods. MURF-1 is localized to filamentous microtubules of the cytoskeleton in C2 myotubes.

FIGS. 4A–C. Hela cells were transfected with myc-tagged MURF and immunofluorescence performed. MURF-1 (green) forms filaments that directly colocalize with microtubules (red) as seen in panel C. Yellow color in C is the result of direct overlap of MURF-1 and microtubule localization. FIG. 4D. Summary of the microtubule binding domain of MURF-1. The leucine-rich coiled-coil domain mediates microtubule interaction and the RING-finger is required for filament formation. FIG. 4E. Deletion of the N-terminal 16 amino acids alters the undular filaments to a more angular assembly. FIG. 4F. The RING-finger domain is required for filament formation. FIG. 4G. Deletion of the C-terminal acidic domain does not affect microtubule interaction nor filament formation. Cos cells were used in FIGS. 4E and 4G. Identical results were obtained in multiple cell types.

FIG. 5A. Schematic representation of the experimental protocol used in the in vitro microtubule cosedimentation assay. 293T cells treated with nocodazole were transfected with various myc-tagged versions of MURF-1 and soluble extracts prepared. Purified tubulin was added and microtubules were polymerized in the presence of GTP and EGTA. Polymerized microtubules were pelleted and the resulting supernatant was precipitated. The pellet was subjected to depolymerization by calcium and cold treatment. Three cycles of polymerization-depolymerization were repeated before western analysis. FIG. 5B. Representation of MURF-1 deletions used in the analysis. FIG. 5C. Western blot analysis of MURF-1 cosedimentation with microtubules. MURF-1 protein containing the leucine-rich coiled-coil domain cosediments with microtubules. An equivalent amount of MURF-1 mutant N212 is contained in the supernatant and microtubule pellet, lane 5 (*) indicating the amino acids 167–211 are required for optimal microtubule association. The blot was reprobed for tubulin content to assess the extent of microtubule polymerization. Densitometric analysis revealed greater than 90% of the tubulin input was contained in the microtubule pellet.

FIG. 6A. Various forms of N-terminal Flag-tagged MURF-1 and full-length C-terminal myc-tagged MURF-1 were in vitro translated in the presence of $^{35}$S-methionine and immunoprecipitation performed as described in Material and Methods. The leucine-rich coiled-coil domain mediates homo-oligomerization of MURF-1. FIGS. 6B–D. MURF-1 binds to microtubules in a homo-oligomeric form. Hela Cells were transfected with Flag-tagged full-length MURF alone (FIG. 6B) or in combination with myc-tagged MURF-1 (FIGS. 6C and 6D) and immunofluorescence performed. Flag-tagged MURF-1 forms aggregates in the cytoplasm of the cell. In the presence of myc-tagged MURF-1, the Flag-tagged MURF-1 and myc-tagged MURF-1 are colocalized in filamentous structures in the cell. Identical results were obtained using native MURF-1 lacking an epitope tag.

FIGS. 7A–7C. Expression of MURF-1 stabilizes microtubules. Cos cells were transfected with MURF-1 and treated with 2∝M nocodazole for 2 hours and immunofluorescence performed. As seen in panel C, only cells expressing MURF-1 contain intact microtubules following nocodazole treatment. FIG. 7D. Microtubule interaction and filament formation are required for microtubule stabilization. Deletion of the RING-finger domain (mutant N81) abrogating filament formation or the leucine-rich coiled-coil domain (mutant C199) preventing microtubule association ablates the microtubule stabilization function of MURF-1.

FIGS. 8A–8C. MURF-1 expression enhances Glu-tubulin formation. Cos cells were transfected with MURF-1 and immunostained for MURF-1 and Glu-tubulin to detect stable microtubules. In panel C only cells expressing MURF-1 have a microtubule network enriched in Glu-tubulin. FIG. 8D. MURF-1 expression parallels the appearance of Glu-tubulin during skeletal muscle formation in vitro. C2 cells were induced to differentiate for varying lengths of time and western blot analysis performed to detect MURF-1 expression and Glu-tubulin. MURF-1 expression is observed immediately after differentiation is induced. The formation of Glu-tubulin mirrors the appearance of MURF-1 protein. Blotting with an anti-tubulin antibody confirmed equal quantities of protein in each lane.

Figure 10:
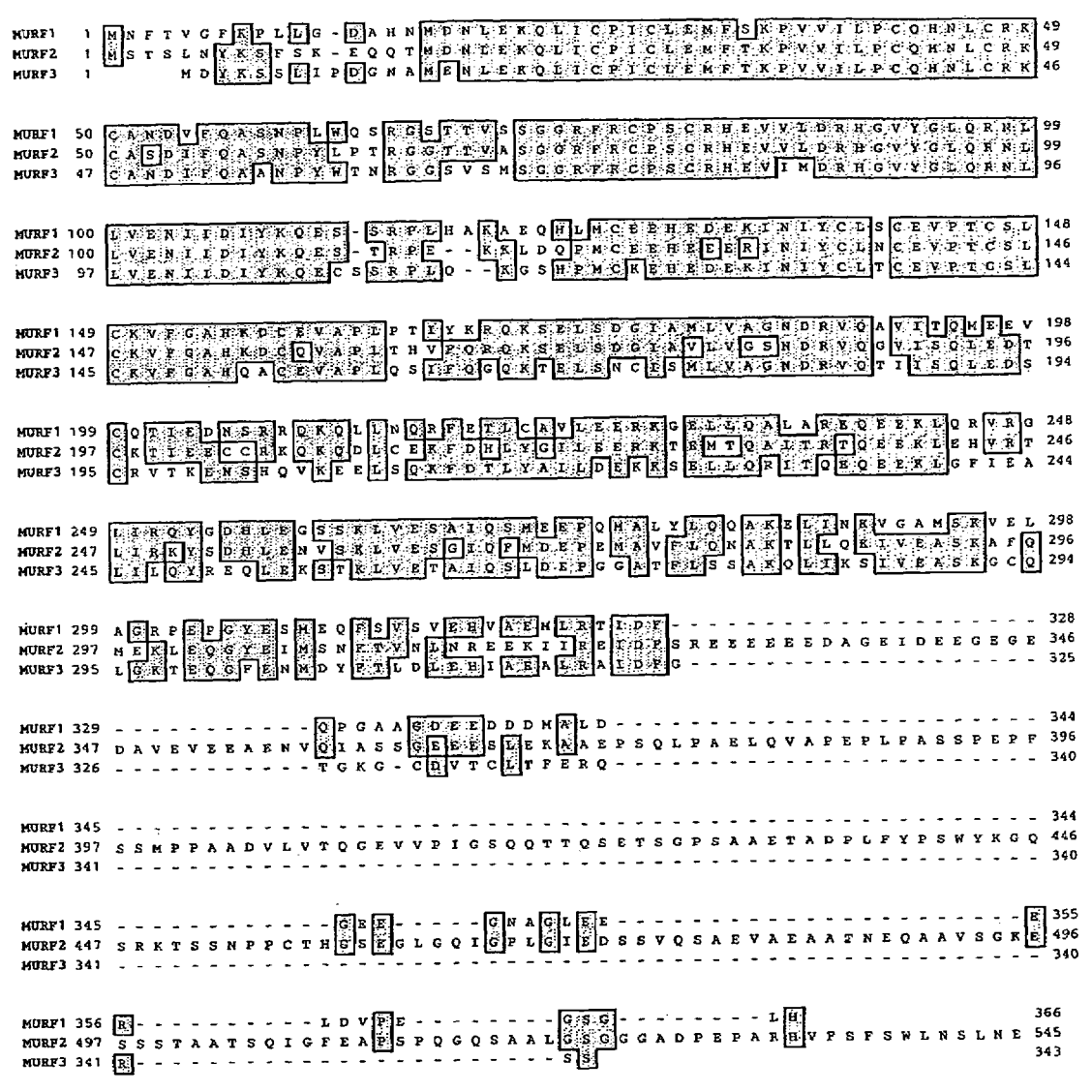

FIG. 10—Alignment of MURF1, MURF2 and MURF3 protein sequences.

DESCRIPTION OF ILLUSTRATIVE EMBODIMENTS

The present inventors describe herein novel RBCC proteins that show significant homology to Midline proteins in the RING-finger and B-box regions. However, this protein is structurally distinct from known Midline proteins, and its expression is restricted to cardiac and skeletal muscle throughout pre- and postnatal development. In particular, MURF1 is down-regulated in cardiomyopathy mouse models, but its overexpression in the heart also results in cardiac dysfunction and death. Like Mid1, MURFs bind and stabilizes microtubules against depolymerizing agents. In addition, MURFs associate with desmin, cytokeratin and vimentin. Thus, MURFs also appear to be general intermediate filament binders. These properties suggest involvement in microtubule and intermediate filament stabilization in striated muscle cells, which is important for alignment of skeletal myoblasts during fusion, myofibrillar assembly, and contractile function. MURFs also hetero-associate with each other, although the precise significance of these interactions is not yet clear.

I. MURF Peptides and Polypeptides

MURF is a designation assigned by the present inventors for Muscle RING Finger proteins. While these molecules are distinct from earlier known polypeptides, they appear to be part of a group of structurally- and functionally-related molecules known as Midline proteins.

In addition to the entire MURF-1, MURF-2 and MURF-3 molecules, the present invention also relates to fragments of the polypeptides that may or may not retain various of the functions described below. Fragments, including the N-terminus of the molecule may be generated by genetic engineering of translation stop sites within the coding region (discussed below). Alternatively, treatment of the MURFs with proteolytic enzymes, known as proteases, can produces a variety of N-terminal, C-terminal and internal fragments. Examples of fragments may include contiguous residues of SEQ ID NOS:2, 4 and 6 of 6, 7, 8, 9, 10, 11, 12, 13, 14, 15, 16, 17, 18, 19, 20, 21, 22, 23, 24, 25, 30, 35, 40, 45, 50, 55, 60, 65, 75, 80, 85, 90, 95, 100, 200, 300, 400 or more amino acids in length. These fragments may be purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

A. Structural Features of the Polypeptide

MURF-1 is 366 amino acid polypeptide. The predicted molecular weight of this molecule is 41 kDa, with a resulting pI of 4.82. Thus, at a minimum, this molecule may be used as a standard in assays where molecule weight and pI are being examined.

Figure 1:
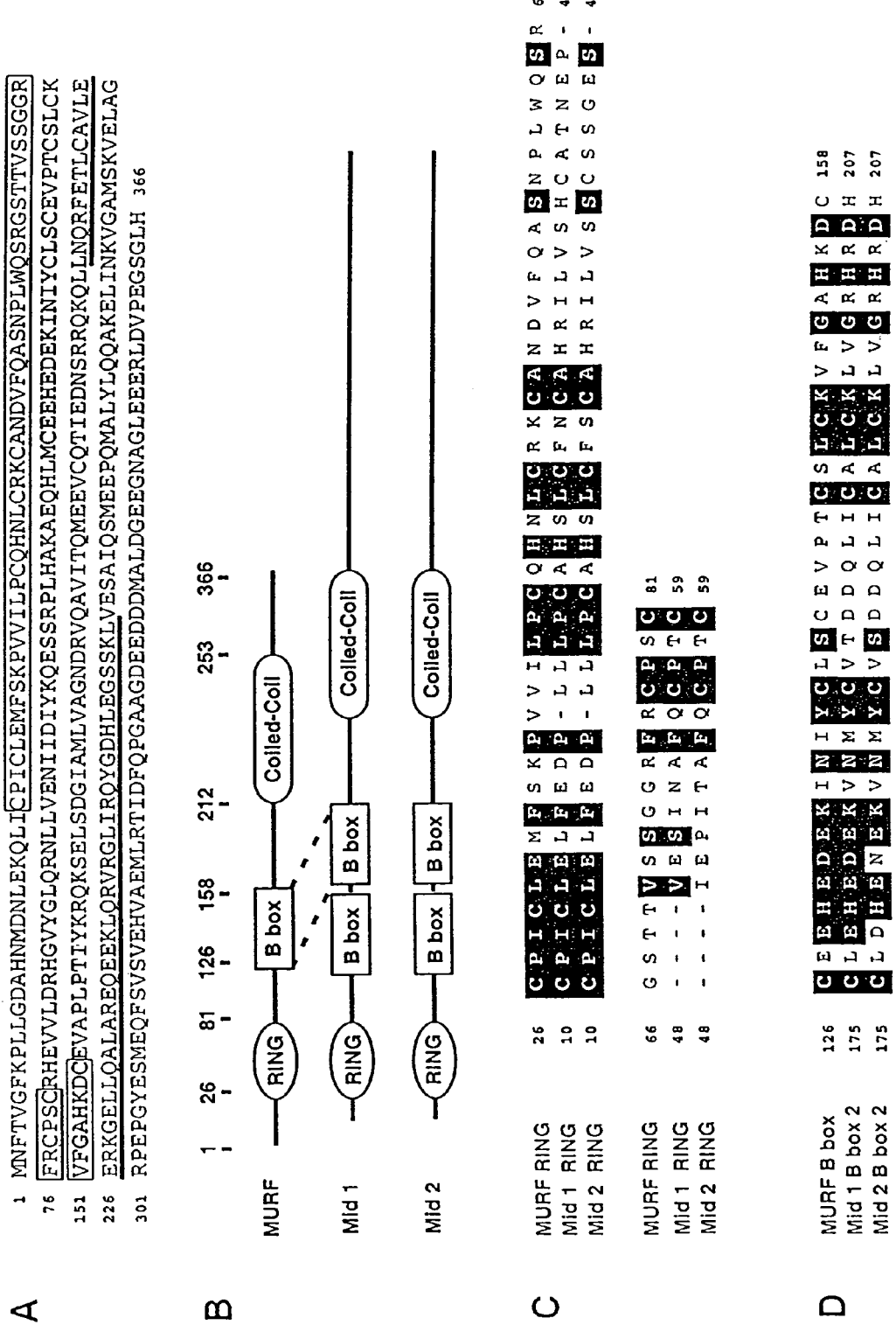
FIGS. 1A–1D—Amino acid sequence of MURF-1 and structural similarity to Midline proteins.

MURF-1 contains several domains that identify it as a RBCC-type of RING-finger protein. A RING-finger of the $C_3HC_4$ type is located near the amino-terminus (amino acids 26–81), followed by another type of zinc-finger termed a B-box (amino acids 126–158) (FIG. 1B). In all other RBBC proteins, the spacing between the RING-finger and B-box is also about 40 amino acids (Borden, 1998; Saurin et al., 1996). A predicted leucine-rich coiled-coil domain (amino acids 212–253) and an acidic region (amino acids 335–366) are located in the C-terminal portion of the protein.

Database searches with the amino acid sequence of MURF-1 revealed highest homology to the Opitz-G/BBB syndrome. protein Mid1 and the related factor Mid2 (FIG. 1C and FIG. 1D) with greatest homology in the RING-finger and B-box domains. Interestingly, MURF-1 does not contain the first B-box of Mid1 and Mid2 nor the butyrophilin-like domain at the C-termini of Mid2 and Mid2, suggesting functional differences between the proteins.

B. Functional Aspects

Although the precise role played my MURFs in cellular physiology is not elucidated, a number of particular functions have been associated with MURF-1. First, MURF-1 binds both to itself (homo-oligomerization) and to microtubules. Microtubule-binding and homo-oligomerization are mediated by the coiled-coil domain at the C-terminus. In addition, MURF-1 plays in role in the formation of microfilaments; this is reliant on the RING-finger domain of MURF-1.

MURF-1 is expressed specifically in cardiac and skeletal tissue. It is downregulated in late stage failing heart, as the heart loses defined structure and contractility. Overexpression of MURF in non-muscle cells inhibits growth, presumably by binding and stabilizing microtubules, the dissociation of which is a prerequisite for mitosis.

The equilibrium of microtubules between the polymerized and depolymerized states influences a variety of cellular processes, including morphological changes, migration, and proliferation. The microtubule-binding properties of MURF are similar in many respects to those of other microtubule associated proteins, such as MAPs, Midline family members, Doublecortin, Lis1, and Tau, which bind and stabilize microtubules (Buchner et al., 1999; Cainarca et al., 1999; Gleeson et al., 1999; Hsieh et al., 1999; Kaech et al., 1996; Kosik, 1990; Koulakoff et al., 1999; Nguyen et al., 1998; Nguyen et al., 1998; Sapir et al., 1997; Sapir et al., 1999; Schweiger et al., 1999; Takemura et al., 1992).

However, MURF lacks a recognizable microtubule association domain commonly contained in MAPs but, instead, associates with microtubules through its leucine-rich coiled-coil domain. Other microtubule binding proteins that lack a classic microtubule association domain found in MAPs also have been identified, including Mid1, Mid2, Doublecortin and Lis1. In this respect, MURF is a member of the non-classical MAPs lacking a consensus microtubule association domain. With the exception of Mid1 and Mid2, most non-classical MAPs do not share significant homology with MURF, suggesting multiple mechanisms for microtubule interaction that may regulate microtubule dynamics in different tissues.

C. Variants of MURFs

Amino acid sequence variants of the polypeptide can be substitutional, insertional or deletion variants. Deletion variants lack one or more residues of the native protein which are not essential for function or immunogenic activity, and are exemplified by the variants lacking a transmembrane sequence described above. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventors that various changes may be made in the DNA sequences of genes without appreciable loss of their biological utility or activity, as discussed below. Table 1 shows the codons that encode particular amino acids.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5), valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure (Johnson et al., 1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of MURF-1, MURF-2 and MURF-3, but with altered and even improved characteristics.

D. Domain Switching

As described in the examples, the present inventors have identified murine MURF-1, MURF-2 and MURF-3. Given the homology with other Midline proteins, an interesting series of mutants can be created by substituting homologous regions of various proteins. This is known, in certain contexts, as "domain switching."

Domain switching involves the generation of chimeric molecules using different but, in this case, related polypeptides. By comparing various Midline proteins, one can make predictions as to the functionally significant regions of these molecules. It is possible, then, to switch related domains of these molecules in an effort to determine the criticality of these regions to MURF-1, MURF-2 and MURF-3 function. These molecules may have additional value in that these "chimeras" can be distinguished from natural molecules, while possibly providing the same function.

Particular structural aspects of MURF-1 that provide fertile ground for domain switching experiments are a RING finger domain (residues 26–81), a B-box (residues 126–158), a leucine-rich coiled-coil (residues 212–253) and an acid region (residues 335–366). These domains may be substituted for related domains of Midline proteins.

E. Fusion Proteins

A specialized kind of insertional variant is the fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of a immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions.

F. Purification of Proteins

It will be desirable to purify MURF-1, MURF-2, MURF-3 or variants thereof Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

G. Synthetic Peptides

The present invention also describes smaller MURF-related peptides for use in various embodiments of the present invention. Because of their relatively small size, the peptides of the invention can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

H. Antigen Compositions

The present invention also provides for the use of MURF-1, MURF-2 and MURF-3 proteins or peptides as antigens for the immunization of animals relating to the production of antibodies. It is envisioned that MURF-1, MURF-2, MURF-3, or portions thereof, will be coupled, bonded, bound, conjugated or chemically-linked to one or more agents via linkers, polylinkers or derivatized amino acids. This may be performed such that a bispecific or multivalent composition or vaccine is produced. It is further envisioned that the methods used in the preparation of these compositions will be familiar to those of skill in the art and should be suitable for administration to animals, i.e., pharmaceutically acceptable. Preferred agents are the carriers are keyhole limpet hemocyannin (KLH) or bovine serum albumin (BSA).

III. Nucleic Acids

The present invention also provides, in another embodiment, genes encoding MURF-1, MURF-2 and MURF-3. Genes for murine MURF-1, MURF-2 and MURF-3 have been identified. The present invention is not limited in scope to these genes, however, as one of ordinary skill in the could, using these nucleic acids, readily identify related homologs in various other species (e.g., rat, rabbit, dog, monkey, gibbon, human, chimp, ape, baboon, cow, pig, horse, sheep, cat and other species).

In addition, it should be clear that the present invention is not limited to the specific nucleic acids disclosed herein. As discussed below, a "MURF gene" may contain a variety of different bases and yet still produce a corresponding polypeptide that is functionally indistinguishable, and in some cases structurally, from the human and mouse genes disclosed herein.

Similarly, any reference to a nucleic acid should be read as encompassing a host cell containing that nucleic acid and, in some cases, capable of expressing the product of that nucleic acid. In addition to therapeutic considerations, cells expressing nucleic acids of the present invention may prove useful in the context of screening for agents that induce, repress, inhibit, augment, interfere with, block, abrogate, stimulate or enhance the function of MURF-1, MURF-2 or MURF-3.

A. Nucleic Acids Encoding MURFs

Nucleic acids according to the present invention may encode an entire MURF-1, MURF-2 or MURF-3 gene, a domain of MURF-1, MURF-2 or MURF-3, or any other fragment of MURF-1, MURF-2 or MURF-3 as set forth herein. The nucleic acid may be derived from genomic DNA, i.e., cloned directly from the genome of a particular organism. In preferred embodiments, however, the nucleic acid would comprise complementary DNA (cDNA). Also contemplated is a cDNA plus a natural intron or an intron derived from another gene; such engineered molecules are sometime referred to as "mini-genes." At a minimum, these and other nucleic acids of the present invention may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a given MURF from a given species may be represented by natural variants that have slightly different nucleic acid sequences but, nonetheless, encode the same protein (see Table 1 below).

As used in this application, the term "a nucleic acid encoding a MURF" refers to a nucleic acid molecule that has been isolated free of total cellular nucleic acid. In preferred embodiments, the invention concerns a nucleic acid sequence essentially as set forth in SEQ ID NOS: 1 and 3. The term "as set forth in SEQ ID NOS: 1 or 3 or 5" means that the nucleic acid sequence substantially corresponds to a portion of SEQ ID NO:1, 3 or 5. The term "functionally equivalent codon" is used herein to refer to codons that encode the same amino acid, such as the six codons for arginine or serine (Table 1, below), and also refers to codons that encode biologically equivalent amino acids, as discussed in the following pages.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

Allowing for the degeneracy of the genetic code, sequences that have at least about 50%, usually at least about 60%, more usually about 700%, most usually about 80%, preferably at least about 90% and most preferably about 95% of nucleotides that are identical to the nucleotides of SEQ ID NOS:1 or 3 or 5 are contemplated. Sequences that are essentially the same as those set forth in SEQ ID NOS:1, 3 and 5 may also be functionally defined as sequences that are capable of hybridizing to a nucleic acid segment containing the complement of SEQ ID NOS:1, 3 and 5 under standard conditions.

The DNA segments of the present invention include those encoding biologically functional equivalent MURF proteins and peptides, as described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

B. Oligonucleotide Probes and Primers

Naturally, the present invention also encompasses DNA segments that are complementary, or essentially complementary, to the sequence set forth in SEQ ID NOS:1, 3 and 5. Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NOS:1, 3 and 5 under relatively stringent conditions such as those described herein. Such sequences may encode the entire MURF proteins or functional or non-functional fragments thereof.

Alternatively, the hybridizing segments may be shorter oligonucleotides. Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 250, 500, 1000, 1212, 1500, 2000, 2500, 3000 or 5000 bases and longer are contemplated as well. Such oligonucleotides will find use, for example, as probes in Southern and Northern blots and as primers in amplification reactions.

Suitable hybridization conditions will be well known to those of skill in the art. In certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 µM $MgCl_2$, at temperatures ranging from approximately 40° C. to about 72° C. Formamide and SDS also may be used to alter the hybridization conditions.

One method of using probes and primers of the present invention is in the search for genes related to MURF-1, MURF-2 or MURF-3 or, more particularly, homologs of MURF-1, MURF-2 or MURF-3 from other species. Normally, the target DNA will be a genomic or cDNA library, although screening may involve analysis of RNA molecules. By varying the stringency of hybridization, and the region of the probe, different degrees of homology may be discovered.

Another way of exploiting probes and primers of the present invention is in site-directed, or site-specific mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single-stranded and double-stranded form. Typical vectors useful in site-directed mutagenesis include vectors such as the M13 phage. These phage vectors are commercially available and their use is generally well known to those skilled in the art. Double-stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double-stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

C. Antisense Constructs

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50–200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

D. Ribozymes

Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cook, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cook et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cook et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

E. Vectors for Cloning, Gene Transfer and Expression

Within certain embodiments expression vectors are employed to express a MURF polypeptide product, which can then be purified and, for example, be used to vaccinate animals to generate antisera or monoclonal antibody with which further studies may be conducted. In other embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

(i) Regulatory Elements

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

In preferred embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

In various embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. Further, selection of a promoter that is regulated in response to specific physiologic signals can permit inducible expression of the gene product. Tables 2 and 3 list several regulatory elements that may be employed, in the context of the present invention, to regulate the expression of the gene of interest. This list is not intended to be exhaustive of all the possible elements involved in the promotion of gene expression but, merely, to be exemplary thereof Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a gene of interest in an expression construct (Table 2 and Table 3). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 2

Promoter and/or Enhancer

| Promoter/Enhancer | References |
| --- | --- |
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987a |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $\alpha_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |

TABLE 2-continued

Promoter and/or Enhancer

| Promoter/Enhancer | References |
| --- | --- |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987; Glue et al., 1988 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 3

Inducible Elements

| Element | Inducer | References |
| --- | --- | --- |
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

Of particular interest are muscle specific promoters, and more particularly, cardiac specific promoters. These include the myosin light chain-2 promoter (Franz et al., 1994; Kelly et al., 1995), the alpha actin promoter (Moss et al., 1996), the troponin 1 promoter (Bhavsar et al., 1996); the $Na^+/Ca^{2+}$ exchanger promoter (Barnes et al., 1997), the dystrophin promoter (Kimura et al., 1997), the creatine kinase promoter (Ritchie, M. E., 1996), the alpha7 integrin promoter (Ziober & Kramer, 1996), the brain natriuretic peptide promoter (LaPointe et al., 1996), the alpha B-crystallin/small heat shock protein promoter (Gopal-Srivastava, R., 1995), and alpha myosin heavy chain promoter (Yamauchi-Takihara et al., 1989) and the ANF promoter (LaPointe et al., 1988).

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

(ii) Selectable Markers

In certain embodiments of the invention, the cells contain nucleic acid constructs of the present invention, a cell may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

(iii) Multigene Constructs and IRES

In certain embodiments of the invention, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

(iv) Delivery of Expression Vectors

There are a number of ways in which expression vectors may introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986).

One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome. (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors, as described by Karlsson et al (1986), or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{12}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors., Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact-sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al., recently introduced the chloramphenicol acetyltransferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type by any number of receptor-ligand systems with or without liposomes. For example, epidermal growth factor (EGF) may be used as the receptor for mediated delivery of a nucleic acid into cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

IV. Generating Antibodies Reactive with MURFs

In another aspect, the present invention contemplates an antibody that is immunoreactive with a MURF molecule of the present invention, or any portion thereof An antibody can be a polyclonal or a monoclonal antibody. In a preferred embodiment, an antibody is a monoclonal antibody. Means for preparing and characterizing antibodies are well known in the art (see, e.g., Harlow and Lane, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a non-human animal including rabbits, mice, rats, hamsters, pigs or horses. Because of the relatively large blood volume of rabbits, a rabbit is a preferred choice for production of polyclonal antibodies.

Antibodies, both polyclonal and monoclonal, specific for isoforms of antigen may be prepared using conventional immunization techniques, as will be generally known to those of skill in the art. A composition containing antigenic epitopes of the compounds of the present invention can be used to immunize one or more experimental animals, such as a rabbit or mouse, which will then proceed to produce specific antibodies against the compounds of the present invention. Polyclonal antisera may be obtained, after allowing time for antibody generation, simply by bleeding the animal and preparing serum samples from the whole blood.

It is proposed that the monoclonal antibodies of the present invention will find useful application in standard immunochemical procedures, such as ELISA and Western blot methods and in immunohistochemical procedures such as tissue staining, as well as in other procedures which may utilize antibodies specific to MURF-related antigen epitopes. Additionally, it is proposed that monoclonal antibodies specific to the particular MURF of different species may be utilized in other useful applications In general, both polyclonal and monoclonal antibodies against MURFs may be used in a variety of embodiments. For example, they may be employed in antibody cloning protocols to obtain cDNAs or genes encoding other MURFs. They may also be used in inhibition studies to analyze the effects of MURFs related peptides in cells or animals. MURF antibodies will also be useful in immunolocalization studies to analyze the distribution of MURFs during various cellular events, for example, to determine the cellular or tissue-specific distribution of MURF polypeptides under different points in the cell cycle. A particularly useful application of such antibodies is in purifying native or recombinant MURFs, for example, using an antibody affinity column. The operation of all such immunological techniques will be known to those of skill in the art in light of the present disclosure.

Means for preparing and characterizing antibodies are well known in the art (see, e.g., Harlow and Lane, 1988; incorporated herein by reference). More specific examples of monoclonal antibody preparation are given in the examples below.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimido-bencoyl-N-hydroxysuccinimide ester, carbodiimide and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified MURF protein, polypeptide or peptide or cell expressing high levels of MURF. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, P3-X63-Ag8.653, NS1/1.Ag 4 1, Sp210-Ag14, FO, NSO/U, MPC-11, MPC11-X45-GTG 1.7 and S194/5XX0Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al., (1977). The use of electrically induced fusion methods is also appropriate (Goding, 1986).

Fusion procedures usually produce viable hybrids at low frequencies, around $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

V. Diagnosing and Treating Defects in MURFs

The inventors have shown MURFs play an important role in the stabilization of microtubules. In addition, in diseased heart tissue, MURF activity is reduced, implicating that MURFs, possibly through microtubule stabilization, play in important role in normal cardiac function. Thus, in another embodiment, there are provided methods for diagnosing defects in MURF expression and function. More specifically, point mutations, deletions, insertions or regulatory pertubations relating to MURFs may be assessed using standard technologies, as described below.

A. Genetic Diagnosis

One embodiment of the instant invention comprises a method for detecting variation in the expression of MURF-1, MURF-2 or MURF-3. This may comprises determining that level of MURF-1, MURF-2 or MURF-3 or determining specific alterations in the expressed product.

A suitable biological sample can be any tissue or fluid. Various embodiments include cells of the skin, muscle, facia, brain, prostate, breast, endometrium, lung, head & neck, pancreas, small intestine, blood cells, liver, testes, ovaries, colon, skin, stomach, esophagus, spleen, lymph node, bone marrow or kidney. Other embodiments include fluid samples such as peripheral blood, lymph fluid, ascites, serous fluid, pleural effusion, sputum, cerebrospinal fluid, lacrimal fluid, stool or urine.

Nucleic acid used is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Various types of defects may be identified by the present methods. Thus, "alterations" should be read as including deletions, insertions, point mutations and duplications. Point mutations result in stop codons, frameshift mutations or amino acid substitutions. Somatic mutations are those occurring in non-germline tissues. Germ-line tissue can occur in any tissue and are inherited. Mutations in and outside the coding region also may affect the amount of MURF produced, both by altering the transcription of the gene or in destabilizing or otherwise altering the processing of either the transcript (mRNA) or protein.

It is contemplated that other mutations in the MURF genes may be identified in accordance with the present invention. A variety of different assays are contemplated in this regard, including but not limited to, fluorescent in situ hybridization (FISH), direct DNA sequencing, PFGE analysis, Southern or Northern blotting, single-stranded conformation analysis (SSCA), RNAse protection assay, allele-specific oligonucleotide (ASO), dot blot analysis, denaturing gradient gel electrophoresis, RFLP and PCR™-SSCP.

(i) Primers and Probes

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred. Probes are defined differently, although they may act as primers. Probes, while perhaps capable of priming, are designed to binding to the target DNA or RNA and need not be used in an amplification process.

In preferred embodiments, the probes or primers are labeled with radioactive species ($^{32}P$, $^{14}C$, $^{35}S$, $^{3}H$, or other label), with a fluorophore (rhodamine, fluorescein) or a chemillumiscent (luciferase).

(ii) Template Dependent Amplification Methods

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in its entirety.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990. Polymerase chain reaction methodologies are well known in the art.

Another method for amplification is the ligase chain reaction ("LCR"), disclosed in EPO No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Methods based on ligation of two (or more) oligonucleotides in the presence of nucleic acid having the sequence of the resulting "di-oligonucleotide", thereby amplifying the di-oligonucleotide, may also be used in the amplification step of the present invention. Wu et al., (1989), incorporated herein by reference in its entirety.

(iii) Southern/Northern Blotting

Blotting techniques are well known to those of skill in the art. Southern blotting involves the use of DNA as a target, whereas Northern blotting involves the use of RNA as a target. Each provide different types of information, although cDNA blotting is analogous, in many aspects, to blotting or RNA species.

Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will binding a portion of the target sequence under renaturing conditions. Unbound probe is then removed, and detection is accomplished as described above.

(iv) Separation Methods

It normally is desirable, at one stage or another, to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

(v) Detection Methods

Products may be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by a labeled probe. The techniques involved are well known to those of skill in the art and can be found in many standard books on molecular protocols. See Sambrook et al., 1989. For example, chromophore or radiolabel probes or primers identify the target during or following amplification.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

In addition, the amplification products described above may be subjected to sequence analysis to identify specific kinds of variations using standard sequence analysis techniques. Within certain methods, exhaustive analysis of genes is carried out by sequence analysis using primer sets designed for optimal sequencing (Pignon et al, 1994). The present invention provides methods by which any or all of these types of analyses may be used. Using the sequences disclosed herein, oligonucleotide primers may be designed to permit the amplification of sequences throughout the MURF genes that may then be analyzed by direct sequencing.

(vi) Kit Components

All the essential materials and reagents required for detecting and sequencing MURF-1, MURF-2 and MURF-3 and variants. thereof may be assembled together in a kit. This generally will comprise preselected primers and probes. Also included may be enzymes suitable for amplifying nucleic acids including various polymerases (RT, Taq, Sequenase™ etc.), deoxynucleotides and buffers to provide the necessary reaction mixture for amplification. Such kits also generally will comprise, in suitable means, distinct containers for each individual reagent and enzyme as well as for each primer or probe.

B. Immunologic Diagnosis

Antibodies of the present invention can be used in characterizing the MURF content of healthy and diseased tissues, through techniques such as ELISAs and Western blotting. This may provide a screen for the presence or absence of cardiomyopathy or as a predictor of heart disease.

The use of antibodies of the present invention, in an ELISA assay is contemplated. For example, anti-MURF antibodies are immobilized onto a selected surface, preferably a surface exhibiting a protein affinity such as the wells of a polystyrene microtiter plate. After washing to remove incompletely adsorbed material, it is desirable to bind or coat the assay plate wells with a non-specific protein that is known to be antigenically neutral with regard to the test antisera such as bovine serum albumin (BSA), casein or solutions of powdered milk. This allows for blocking of non-specific adsorption sites on the immobilizing surface and thus reduces the background caused by non-specific binding of antigen onto the surface.

After binding of antibody to the well, coating with a non-reactive material to reduce background, and washing to remove unbound material, the immobilizing surface is contacted with the sample to be tested in a manner conducive to immune complex (antigen/antibody) formation.

Following formation of specific immunocomplexes between the test sample and the bound antibody, and subsequent washing, the occurrence and even amount of immunocomplex formation may be determined by subjecting same to a second antibody having specificity for MURF-1, MURF-2 or MURF-3 that differs the first antibody. Appropriate conditions preferably include diluting the sample with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hr, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

To provide a detecting means, the second antibody will preferably have an associated enzyme that will generate a color development upon incubating with an appropriate chromogenic substrate. Thus, for example, one will desire to contact and incubate the second antibody-bound surface with a urease or peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody.

The antibody compositions of the present invention will find great use in immunoblot or Western blot analysis. The antibodies may be used as high-affinity primary reagents for the identification of proteins immobilized onto a solid support matrix, such as nitrocellulose, nylon or combinations thereof In conjunction with immunoprecipitation, followed by gel electrophoresis, these may be used as a single step reagent for use in detecting antigens against which secondary reagents used in the detection of the antigen cause an adverse background. Immunologically-based detection methods for use in conjunction with Western blotting include enzymatically-, radiolabel-, or fluorescently-tagged secondary antibodies against the toxin moiety are considered to be of particular use in this regard.

C. Treating Defects in MURF Expression or Function

The present invention also involves, in another embodiment, the treatment of disease states related to the aberrant expression and/or function of MURFs. In particular, it is envisioned that reduced MURF activity plays a role in microtubule destabilization and cardiac failure. Thus, increasing levels of MURFs, or compensating for mutations that reduce or eliminate the activity of MURFs, are believed to provide therapeutic intervention in cardiomyopathies.

In addition, by increasing levels of MURFs, it is possible that defects in other cardiac genes may be compensated for. As discussed above, MURFs bind to and stabilize microtubules. Thus, increasing the expression of MURFs can stabilize the cytoskeleton of failing heart. Similarly, in situations where increase heart muscle mass is desired, inhibiting MURF expression could stimulate proliferation.

D. Genetic Based Therapies

One of the therapeutic embodiments contemplated by the present inventors is the intervention, at the molecular level, in the events involved in cardiac failure. Specifically, the present inventors intend to provide, to a cardiac cell, an expression construct capable of providing MURF-1, MURF-2 or MURF-3 to that cell. Because the sequence homology between the human, mouse and *Drosophila* genes, any of these nucleic acids could be used in human therapy, as could any of the gene sequence variants discussed above which would encode the same, or a biologically equivalent polypeptide. The lengthy discussion of expression vectors and the genetic elements employed therein is incorporated into this section by reference. Particularly preferred expression vectors are viral vectors such as adenovirus, adeno-associated virus, herpesvirus, vaccinia virus and retrovirus. Also preferred is liposomally-encapsulated expression vector.

Those of skill in the art are well aware of how to apply gene delivery to in vivo situations. For viral vectors, one generally will prepare a viral vector stock. Depending on the kind of virus and the titer attainable, one will deliver $1\times10^4$, $1\times10^5$, $1\times10^6$, $1\times10^7$, $1\times10^8$, $1\times10^9$, $1\times10^{10}$, $1\times10^{11}$ or $1\times10^{12}$ infectious particles to the patient. Similar figures may be extrapolated for liposomal or other non-viral formulations by comparing relative uptake efficiencies. Formulation as a pharmaceutically acceptable composition is discussed below. Various routes are contemplated, but local provision to the heart and systemic provision (intraarterial or intravenous) are preferred.

E. Combined Therapy

In many clinical situations, it is advisable to use a combination of distinct therapies. Thus, it is envisioned that, in addition to the therapies described above, one would also wish to provide to the patient more "standard" pharmaceutical cardiac therapies. Examples of standard therapies include so-called "beta blockers", anti-hypertensives, cardiotonics, anti-thrombotics, vasodilators, hormone antagonists, endothelin antagonists, cytokine inhibitors/blockers, calcium channel blockers, phosphodiesterase inhibitors and angiotensin type 2 antagonists. Also envisioned are combinations with pharmaceuticals identified according to the screening methods described herein.

Combinations may be achieved by contacting cardiac cells with a single composition or pharmacological formulation that includes both agents, or by contacting the cell with two distinct compositions or formulations, at the same time, wherein one composition includes the expression construct and the other includes the agent. Alternatively, gene therapy may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would contact the cell with both modalities within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either a MURF-1, MURF-2 or MURF-3 gene, or the other agent will be desired. Various combinations may be employed, where MURF is "A" and the other agent is "B", as exemplified below:

```
A/B/A   B/A/B   B/B/A   A/A/B   B/A/A   A/B/B   B/B/B/A  B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B
```

Other Combinations are Contemplated as Well.

F. Formulations and Routes for Administration to Patients

Where clinical applications are contemplated, it will be necessary to prepare pharmaceutical compositions—expression vectors, virus stocks and drugs—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

VI. Methods of Making Transgenic Mice

A particular embodiment of the present invention provides transgenic animals that contain MURF-related constructs. Transgenic animals expressing MURF-1 and MURF-2, recombinant cell lines derived from such animals, and transgenic embryos may be useful in methods for screening for and identifying agents that modulate the function of MURF-1 or MURF-2, and thereby alleviate pathology related to the over or under expression of these molecules. The use of constitutively expressed MURFs provides a model for over- or unregulated expression. Also, transgenic animals which are "knocked out" for MURF-1 and/or MURF-2 will find use in analysis of developmental aspects of MURFs.

A. Methods of Producing Transgenics

In a general aspect, a transgenic animal is produced by the integration of a given transgene into the genome in a manner that permits the expression of the transgene. Methods for producing transgenic animals are generally described by Wagner and Hoppe (U.S. Pat. No. 4,873,191; which is incorporated herein by reference), Brinster et al. 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

Typically, a gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish.

DNA clones for microinjection can be prepared by any means known in the art. For example, DNA clones for microinjection can be cleaved with enzymes appropriate for removing the bacterial plasmid sequences, and the DNA fragments electrophoresed on 1% agarose gels in TBE buffer, using standard techniques. The DNA bands are visualized by staining with ethidium bromide, and the band containing the expression sequences is excised. The excised band is then placed in dialysis bags containing 0.3 M sodium acetate, pH 7.0. DNA is electroeluted into the dialysis bags, extracted with a 1:1 phenol:chloroform solution and precipitated by two volumes of ethanol. The DNA is redissolved in 1 ml of low salt buffer (0.2 M NaCl, 20 mM Tris, pH 7.4, and 1 mM EDTA) and purified on an Elutip-D™ column. The column is first primed with 3 ml of high salt buffer (1 M NaCl, 20 mM Tris, pH 7.4, and 1 mM EDTA) followed by washing with 5 ml of low salt buffer. The DNA solutions are passed through the column three times to bind DNA to the column matrix. After one wash with 3 ml of low salt buffer, the DNA is eluted with 0.4 ml high salt buffer and precipitated by two volumes of ethanol. DNA concentrations are measured by absorption at 260 nm in a UV spectrophotometer. For microinjection, DNA concentrations are adjusted to 3 µg/ml in 5 mM Tris, pH 7.4 and 0.1 mM EDTA.

Other methods for purification of DNA for microinjection are described in Hogan et al. *Manipulating the Mouse Embryo* (Cold Spring Harbor Laboratory, Cold Spring Harbor, N.Y., 1986), in Palmiter et al. *Nature* 300:611 (1982); in *The Qiagenologist, Application Protocols,* 3rd edition, published by Qiagen, Inc., Chatsworth, Calif.; and in Sambrook et al. *Molecular Cloning: A Laboratory Manual* (Cold Spring Harbor Laboratory, Cold Spring Harbor, N.Y., 1989).

In an exemplary microinjection procedure, female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG, Sigma). Females are placed with males immediately after hCG injection. Twenty-one hours after hCG injection, the mated females are sacrificed by $CO_2$ asphyxiation or cervical dislocation and embryos are recovered from excised oviducts and placed in Dulbecco's phosphate buffered saline with 0.5% bovine serum albumin (BSA, Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection. Embryos can be implanted at the two-cell stage.

Randomly cycling adult female mice are paired with vasectomized males. C57BL/6 or Swiss mice or other comparable strains can be used for this purpose.

Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS (Dulbecco's phosphate buffered saline) and in the tip of a transfer pipet (about 10 to 12 embryos). The pipet tip is inserted into the infundibulum and the embryos transferred. After the transfer, the incision is closed by two sutures.

B. Disease Models

Microtubule depolymerization is also required for mitosis. Thus, the ability of MURF to prevent microtubule depolymerization is particularly intriguing in that striated muscle cells are irreversibly postmitotic. In this regard, MURF-transfected cells are unable to divide. Thus, it is contemplated that MURF trangenics can be useful to explore pathologies related to microtubule depolymerization and cell division. In addition, it may be possible to screen MURF transfected cells for compounds (peptides, combinatorial chemical libraries) with the potential to stimulate DNA synthesis. Such compounds would have utility in promoting cardiomyocyte proliferation and thereby benefit cardiac regeneration in response to damage.

Microtubules have been shown to play important roles in regulating muscle cell morphology, sarcomere assembly, and function. In skeletal muscle cells, the microtubule network is reorganized to form stable microtubules during differentiation (Gunderson et al., 1989). Integrity of the microtubular array is essential for proper alignment of myoblasts during fusion and for correct formation of myofibrils (Antin et al., 1981; Toyama et al., 1982).

Consistent with the conclusion that MURF is an integral component of the mechanism that regulates microtubule stability in muscle cells, both skeletal and cardiac muscle have been demonstrated to possess a population of microtubules that is stable to depolymerization and cold shock (Webster, 1997). Moreover, expression of MURF mirrors the accumulation of stable glutamic acid-modified tubulin during the formation of skeletal muscle in vitro. A muscle-specific isoform of MAP4 also is expressed upon differentiation in a pattern very similar to that of MURF (Mangan and Olmsted, 1996). However, inhibition of MAP4 expression during differentiation does not block myotube formation but causes the accumulation of multinucleated myotubes with a rounded morphology.

Microtubule stabilization and increased microtubule density also have been proposed as a mechanism for contractile dysfunction in cardiac hypertrophy (Sato et al., 1997). There is evidence that stabilization of the microtubule array in hypertrophic cardiomyocytes is mediated by a microtubule-associated protein, that is as yet unidentified (Sato et al., 1997). MAP4 expression has been demonstrated to be induced during pressure overload-induced hypertrophy in cats (Sato et al., 1997). MAP4 has been demonstrated to stabilize microtubules in vitro making it a plausable candidate for such a factor (Kaech et al., 1996; Nguyen et al., 1997). Interestingly, inhibiting expression of MAP4 in fibroblasts does not adversely affect microtubule dynamics, suggesting a specialized role for MAP4 in a muscle environment or functional redundancy between members of the MAP family (Wang et al., 1996). The striated muscle restricted expression pattern and the microtubule stabilizing effects of MURF make it an interesting candidate for a factor contributing to the contractile dysfunction in cardiac hypertrophy.

VII. Screening Assays

Several human diseases have been linked to mutations in genes encoding microtubule binding proteins, demonstrating the importance of the microtubule network for normal patterning and development. For example, Mid1, Doublecortin, Lis1, and Tau, all microtubule-associated factors capable of stabilizing microtubules, have been implicated in the progression of disease (Gleeson et al., 1999; Kosik, 1990; Koulakoff et al., 1999; Lo Nigro et al., 1997; Quaderi et al., 1997; Tolnay and Probst, 1999). Mutant mice lacking the microtubule-binding proteins Kif3A and Kif3B of the kinesin superfamily, have also been shown to display situs inversus of the heart and other organs (Marszalek et al., 1999; Takeda et al., 1999). A similar phenotype is observed in mice harboring a deleted ATP binding domain of left-right dynein (Supp et al., 1999).

Thus, the present invention also contemplates the screening of compounds for various abilities to interact and/or affect MURF-1, MURF-2 and MURF-3 expression or function. Particularly preferred compounds will be those useful in inhibiting or promoting the actions of MURF-1, MURF-2 and MURF-3 on microtubules (e.g., tubulin) cardiac hypertrophy and preventing or reversing heart disease. In the screening assays of the present invention, the candidate substance may first be screened for basic biochemical activity—e.g., binding to a target molecule—and then tested for its ability to inhibit modulate expression, at the cellular, tissue or whole animal level.

A. Modulators and Assay Formats i) Assay Formats

The present invention provides methods of screening for modulators of MURF-1, MURF-2 and MURF-3 expression and binding to microtubules. In one embodiment, the present invention is directed to a method of (i) providing a MURF-1, MURF-2 or MURF-3 polypeptide;
(ii) contacting the MURF-1, MURF-2 or MURF-3 polypeptide with the candidate substance; and
(iii) determining the binding of the candidate substance to the MURF-1, MURF-2 or MURF-3 polypeptide.

In another embodiment, this assay can be easily modified to look at the candidate substances effects on MURF-1, MURF-2 and/or MURF-3 binding to microtubules, intermediate filaments or homo- or heterodimerization.

In yet another embodiment, the assay looks not at binding, but at MURF function. Such methods would comprise, for example:

(i) providing a cell that expresses MURF-1, MURF-2 or MURF-3 polypeptide;
(ii) contacting the cell with the candidate substance; and
(iii) determining the effect of the candidate substance on glutamic acid modification of microtubules.

In still yet other embodiments, one would look at the effect of a candidate substance on the expression of MURFs. This can be done by examining mRNA expression, although alterations in mRNA stability and translation would not be accounted for. A more direct way of assessing expression is by directly examining protein levels, for example, through Western blot or ELISA.

ii) Inhibitors and Activators

An inhibitor according to the present invention may be one which exerts an inhibitory effect on the expression of function of MURF-1, MURF-2 and/or MURF-3. By the same token, an activator according to the present invention may be one which exerts a stimulatory effect on the expression of function of MURF-1, MURF-2 and/or MURF-3.

iii) Candidate Substances

As used herein, the term "candidate substance" refers to any molecule that may potentially modulate MURF-1, MURF-2 and/or MURF-3 expression or function. The candidate substance may be a protein or fragment thereof, a small molecule inhibitor, or even a nucleic acid molecule. It may prove to be the case that the most useful pharmacological compounds will be compounds that are structurally related to compounds which interact naturally with MURF-1, MURF-2 and/or MURF-3. Creating and examining the action of such molecules is known as "rational drug design," and include making predictions relating to the structure of target molecules.

The goal of rational drug design is to produce structural analogs of biologically active polypeptides or target compounds. By creating such analogs, it is possible to fashion drugs which are more active or stable than the natural molecules, which have different susceptibility to alteration or which may affect the function of various other molecules. In one approach, one would generate a three-dimensional structure for a molecule like a MURF, and then design a molecule for its ability to interact with MURF. Alternatively, one could design a partially functional fragment of a MURF (binding but no activity), thereby creating a competitive inhibitor. This could be accomplished by x-ray crystallography, computer modeling or by a combination of both approaches.

It also is possible to use antibodies to ascertain the structure of a target compound or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds or may be found as active combinations of known compounds which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be polypeptide, polynucleotide, small molecule inhibitors or any other compounds that may be designed through rational drug design starting from known inhibitors of hypertrophic response.

Other suitable inhibitors include antisense molecules, ribozymes, and antibodies (including single chain antibodies).

It will, of course, be understood that all the screening methods of the present invention are useful in themselves notwithstanding the fact that effective candidates may not be found. The invention provides methods for screening for such candidates, not solely methods of finding them.

B. In Vitro Assays

A quick, inexpensive and easy assay to run is a binding assay. Binding of a molecule to a target may, in and of itself, be inhibitory, due to steric, allosteric or charge-charge interactions. This can be performed in solution or on a solid phase and can be utilized as a first round screen to rapidly eliminate certain compounds before moving into more sophisticated screening assays. In one embodiment of this kind, the screening of compounds that bind to a MURF-1, MURF-2 or MURF-3 molecule or fragment thereof is provided.

The target may be either free in solution, fixed to a support, expressed in or on the surface of a cell. Either the target or the compound may be labeled, thereby permitting determining of binding. In another embodiment, the assay may measure the inhibition of binding of a target to a natural or artificial substrate or binding partner (such as a MURF). Competitive binding assays can be performed in which one of the agents (MURF for example) is labeled. Usually, the target will be the labeled species, decreasing the chance that the labeling will interfere with the binding moiety's function. One may measure the amount of free label versus bound label to determine binding or inhibition of binding.

A technique for high throughput screening of compounds is described in WO 84/03564. Large numbers of small peptide test compounds are synthesized on a solid substrate, such as plastic pins or some other surface. The peptide test compounds are reacted with, for example, a MURF and washed. Bound polypeptide is detected by various methods.

Purified target, such as a MURF, can be coated directly onto plates for use in the aforementioned drug screening techniques. However, non-neutralizing antibodies to the polypeptide can be used to immobilize the polypeptide to a solid phase. Also, fusion proteins containing a reactive region (preferably a terminal region) may be used to link an active region (e.g., the C-terminus of a MURF) to a solid phase.

C. In Cyto Assays

Various cell lines that express MURF-1, MURF-2 and or MURF-2 can be utilized for screening of candidate substances. For example, cells containing a MURF with an engineered indicators can be used to study various functional attributes of candidate compounds. In such assays, the compound would be formulated appropriately, given its biochemical nature, and contacted with a target cell.

Depending on the assay, culture may be required. As discussed above, the cell may then be examined by virtue of a number of different physiologic assays (growth, size, $Ca^{++}$ effects). Alternatively, molecular analysis may be performed in which the function of a MURF and related pathways may be explored. This involves assays such as those for protein expression, enzyme function, substrate utilization, mRNA expression (including differential display of whole cell or polyA RNA) and others.

D. In Vivo Assays

The present invention particularly contemplates the use of various animal models. Transgenic animals may be created with constructs that permit MURF expression and activity to be controlled and monitored. The generation of these animals has been described elsewhere in this document.

Treatment of these animals with test compounds will involve the administration of the compound, in an appropriate form, to the animal. Administration will be by any route the could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply.

E. Production of Inhibitors

In an extension of any of the previously described screening assays, the present invention also provide for method of producing inhibitors. The methods comprising any of the preceding screening steps followed by an additional step of "producing the candidate substance identified as a modulator of" the screened activity.

VIII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Material and Methods

Yeast two hybrid screen. Yeast two-hybrid screens of an adult mouse heart cDNA library were performed using full-length serum response factor (SRF) fused to the GAL4 DNA binding domain, as described previously (Spencer et al., 1999). Plasmids were isolated and transformed into electrocompetent XL1-Blue *E. coli*. Plasmids were prepared by alkaline lysis extraction and sequenced. Sequence analysis and comparison was performed using the NCBI web site Blast program.

Mammalian expression plasmid construction. Full-length MURF-1 expression plasmids and C-terminal deletion mutants were constructed by PCR using Expand High Fidelity polymerase (Roche) and cloned in-frame into vector pcDNA3.1 myc/HIS (Invitrogen) or pECE-Flag. N-terminal deletion mutants were constructed by PCR, generating an initiator methionine at desired positions and cloned into the SacII and HindIII sites of full-length MURF-1 in vector pcDNA3.1 myc/HIS. The SacII site is immediately downstream of the Kozak translation initiation sequence contained in the MURF-1 cDNA. The Flag-tagged versions of MURF were subcloned into pcDNA3.1 for use in in vitro analyses.

Radioactive in situ hybridization. RNA probes corresponding to the sense and antisense strands of the MURF-1 cDNA were prepared using T7 RNA polymerase (Roche). In situ hybridization was performed as previously described (Benjamin et al., 1997).

Cell culture, transfection, alkaloid treatment, and immunofluorescence. Cos-1, Hela, 10T1/2, 293, 3T3 and 293T cells were maintained in DMEM supplemented with 10% heat-inactivated fetal bovine serum (FBS). C2 cells were maintained in DMEM containing 20% heat-inactivated FBS. Cells were transfected with 1 µg of various MURF-1 expression plasmids using Fugene6 reagent as recommended by the manufacturer (Roche). 293 T cells were transfected using the calcium phosphate coprecipitation technique (Spencer and Misra, 1996). Cells were treated for 2 hours with 2 µM nocodazole (Sigma) or 2 µM cytochalasin D (Sigma) as indicated.

For immunofluorescence, cells were extracted with 1% Triton X-100 in PBS for 1 minute, washed twice in PBS, and fixed for 15 minutes in 3.7% formalin in PBS. Cells were then washed three times in PBS and blocked in PBS containing 3% Bovine Serum Albumin and 0.1% NP40 for 30 minutes. All antibodies were incubated in fresh block solution for 60 minutes at ambient temperature. Myc-tagged versions of MURF-1 were detected using antibody 9E10 (Santa Cruz) at a dilution of 1:250. Flag-tagged versions of MURF-1 were detected using the M2 Flag antibody at a dilution of 1:500 (Kodak). Microtubules were detected using alpha-tubulin antibody at a dilution of 1:2000 (Sigma). Intermediate filaments were visualized using vimentin antibody at a dilution of 1:500 (Sigma). Actin was visualized using Rhodamine-conjugated phalloidin (Sigma). Secondary antibodies were purchased from Vector labs and used at a dilution of 1:400 in fresh block solution. C2 cells were treated as described above except the polyclonal antibody UT82, raised against MURF-1, was used at a dilution of 1:500.

In vitro transcription/translation and immunoprecipitation. In vitro transcription/translation was performed as directed by the manufacturer (Promega). Plasmids used were C-terminally myc-tagged full-length MURF-1 and various Flag-tagged deletions of MURF-1. Immunoprecipitations were performed using $^{35}$S-methionine-labelled in vitro translation products. Briefly, $^{35}$S-methionine-labelled products were incubated with agitation in 1 ml of immuno-precipitation buffer (PBS, 0.5% Triton X-100, 0.25 mM zinc sulphate) at 4° C. for 2 hours. 2.5 µl of the Flag-antibody M2 was added and incubated an additional 60 minutes. 40 µl of protein A/G-plus beads (Santa Cruz) were added and incubated 30 minutes. Reactions were centrifuged at 2500 rpm for 5 minutes at 4° C. Pellets were washed with rocking for 5 minutes in 1 ml of immunoprecipitation buffer. Washing was repeated 4 times before resuspension of the pellet in 20 µl of SDS-sample buffer. Approximately 10 µl was used in SDS-PAGE analysis. Gels were dried under vacuum and results were visualized by autoradiography.

Northern blot analysis, RNA isolation and RT-PCR. Northern blot analysis was performed using a multiple tissue Northern blot from Clontech and $^{32}$P-labeled probe made from the MURF-1 full-length cDNA. Hybridization was performed for 1 h using rapid-hybe buffer (Amersham). C2 cells were induced to differentiate by the addition of DMEM supplemented with 2% horse serum. Cells were incubated for various lengths of time and total RNA isolated by TriZol extraction (GIBCO). RT-PCR was performed as described in (Rawls et al., 1998).

UT 82 antibody production. An NcoI-HindIII fragment spanning the coding region for amino acids 271–366 of MURF-1 was fused in-frame into vector pGEX2T-polyG. BL21-DE3 cells containing the GST-fusion expression plasmid were grown to an optical density of 0.5 and induced with 1 mM IPTG for 3 h at 30° C. Cells were pelleted and washed in ice cold PBS. Lysis was induced by sonication and protein was purified by GST-affinity chromatography using standard techniques. Rabbit immunization was conducted at Cocalico Biological.

Western blot. Whole cell extracts from mouse tissues and C2 cells were prepared as described previously (Spencer et al., 1999). Approximately 25 µg of total protein was used in the analysis. MURF UT82 was used at a dilution of 1:4000, anti-Glu-tubulin was used at a dilution of 1:2000, and anti-tubulin was used at a dilution of 1:10,000. Mouse and rabbit HRP-conjugated secondary antibodies were used at. a dilution of 1:5000. Chemiluminescence was detected using Luminol Reagent (Santa Cruz).

Microtubule sedimentation assays. For endogenous MURF-microtubule cosedimentation experiments, two-month old female mice were euthanized by standard protocols, hearts and quadriceps (100 mg each tissue) were removed, and placed in ice cold PBS containing protease inhibitors (Roche) for 20 minutes. Tissue was finely minced and placed in 1 ml of PCM buffer (0.1 M Pipes, pH 6.9, 2.5 mM $CaCl_2$, 1 mM $MgSO_4$, pH 6.9) plus protease inhibitors. This was promptly homogenized in a ground glass Dounce homogenizer with 25–30 strokes on ice. Nuclei and debris were removed by low speed centrifugation (3000 rpm) for 5 minutes at 4° C. The supernatant was centrifuged at 100,000×g for 30 minutes at 4° C. to remove cytoplasmic contaminants. The resulting supernatant was used in the microtubule sedimentation analysis. The supernatant was supplemented with 2 mM GTP and 5 mM EGTA and incubated at 37° C. for 20 minutes. This was layered onto a 25% sucrose cushion in PEM buffer (0.1 M Pipes, 1 mM EGTA, 1 mM $MgSO_4$) plus 1 mM GTP and centrifuged at 20,000×g for 30 minutes at room temperature. The supernatant was removed and acetone precipitated. The pellet was resuspended in PEM buffer minus GTP and supplemented to 2 mM $CaCl_2$. This was placed on ice for 30 min. The second polymerization was induced by adding EGTA and GTP to 5 mM and 1 mM, respectively, and incubation at 37° C. Polymerization-depolymerization was repeated 3 times to avoid cytoplasmic contamination. The final polymerization was induced as described above and supplemented with 20 µM taxol (Sigma). The resulting microtubule pellet was resuspended in 50 µl of PEM. Approximately 25 µg of protein was used for western analysis. For microtubule sedimentation assays using transfected cells, cells were harvested and treated as described in (Kaufman et al., 1999).

Example 2

Results

Figure 2:
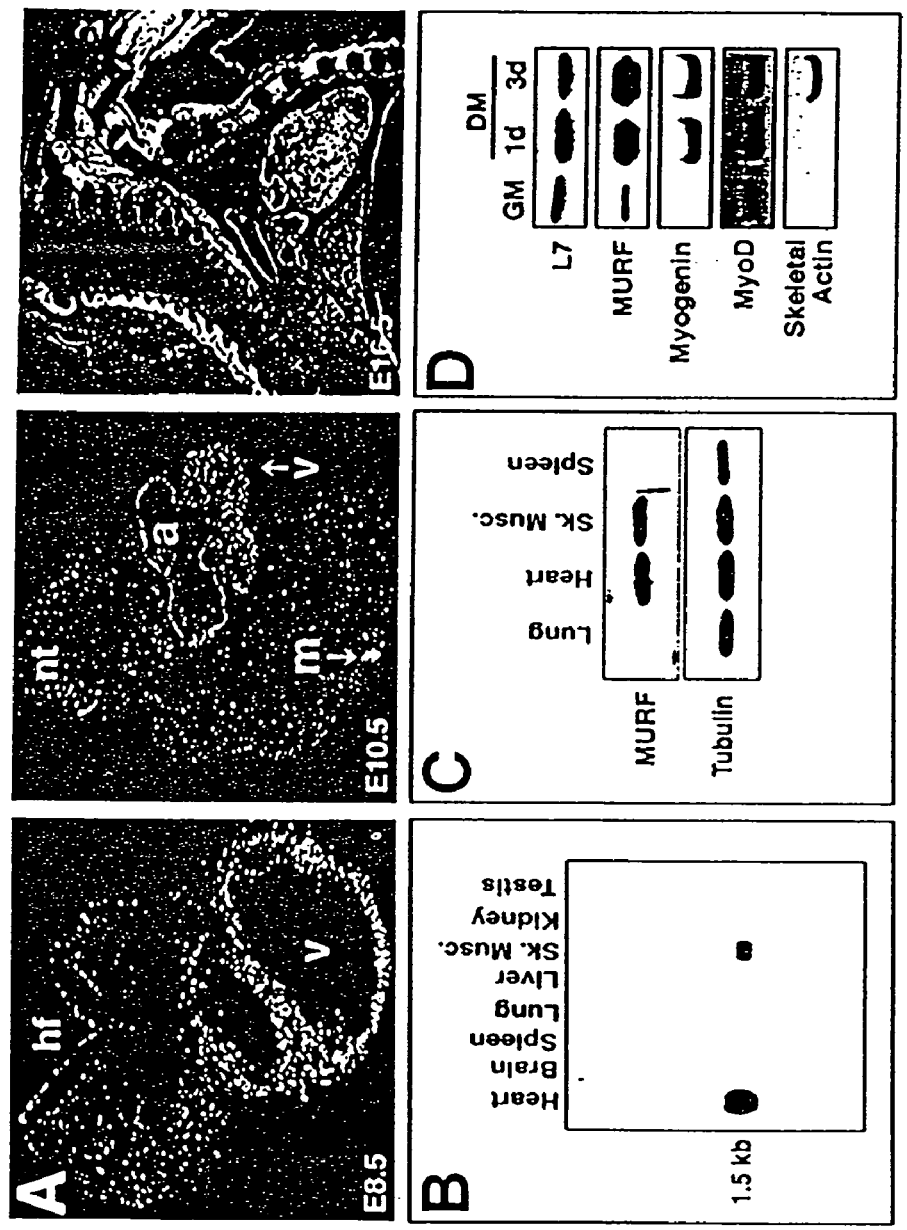
FIGS. 2A–2D—Muscle-specific expression of MURF-1 RNA and protein.

Isolation of MURF-1 cDNA. In a two-hybrid screen for cardiac factors that interact with serum response factor (SRF), the inventors identified a cDNA encoding a novel muscle-specific RING-finger protein, which the inventors named MURF-1 (Muscle RING Finger). Subsequent attempts to demonstrate interaction between SRF and MURF-1, or colocalization of the proteins in mammalian cells, were unsuccessful. Thus, the inventors do not believe this interaction is biologically significant, but it may reflect an ability of SRF to interact with other RING-finger proteins, as several such proteins have been shown to regulate transcription (Hsieh et al., 1999). Nevertheless, because of its interesting structure and expression pattern (see FIG. 2), the inventors continued to characterize MURF-1.

The MURF-1 cDNA encodes a 366 amino acid protein with a predicted molecular weight of 41 kDa and pI of 4.82 (FIG. 1A, Accession number). MURF-1 contains several domains that identify it as a RBCC-type of RING-finger protein. A RING-finger of the $C_3HC_4$ type is located near the amino-terminus (amino acids 26–81), followed by another type of zinc-finger termed a B-box (amino acids 126–158) (FIG. 1B). In all other RBBC proteins, the spacing between the RING-finger and B-box is also about 40 amino acids (Borden, 1998; Saurin et al., 1996). A predicted leucine-rich coiled-coil domain (amino acids 212–253) and an acidic region (amino acids 335–366) are located in the C-terminal portion of the protein.

Database searches with the amino acid sequence of MURF-1 revealed highest homology to the Opitz-G/BBB syndrome protein Mid1 and the related factor Mid2 (FIG. 1C and FIG. 1D) with greatest homology in the RING-finger and B-box domains. Interestingly, MURF-1 does not contain the first B-box of Mid1 and Mid2 nor the butyrophilin-like domain at the C-termini of Mid2 and Mid2, suggesting functional differences between the proteins.

MURF-1 expression is restricted to striated muscle. The expression pattern of MURF-1 was examined during mouse embryogenesis by in situ hybridization. At E8.5, MURF-1 expression was observed only in the developing cardiac region and at E10.5 expression was restricted exclusively to the heart and the myotome of the somites which gives rise to skeletal muscle. This muscle-specific expression continued throughout prenatal development, with expression observed in the heart and skeletal muscle of the intercostals, diaphragm, limbs, face, and head (see FIG. 2A).

In adult mice, Northern analysis showed a single MURF-1 transcript of about 1.5 kB in cardiac and skeletal muscle (FIG. 2B). Extended exposures (greater than 6 days) revealed a very low level of expression in the lung and brain. Consistent with the restricted expression of MURF-1 mRNA, Western blot analysis of protein from mouse heart, quadriceps, spleen and lung, using anti-MURF antibody, detected MURF-1 protein only in heart and skeletal muscle (FIG. 2C). The size of the protein, 41 kDa, was in agreement with the size predicted from the open reading frame.

The inventors also examined expression of MURF-1 during differentiation of the C2 skeletal muscle cell line. As shown in FIG. 2D, MURF-1 transcripts, measured by semi-quantitative RT-PCR, were upregulated during myoblast differentiation, in parallel with MyoD and myogenin. Interestingly, MURF-1 expression was observed prior to the expression of the muscle structural gene skeletal α-actin, suggesting an early role for MURF-1 in myogenesis. This is consistent with expression observed in the myotome (see FIG. 2A).

Figure 3:
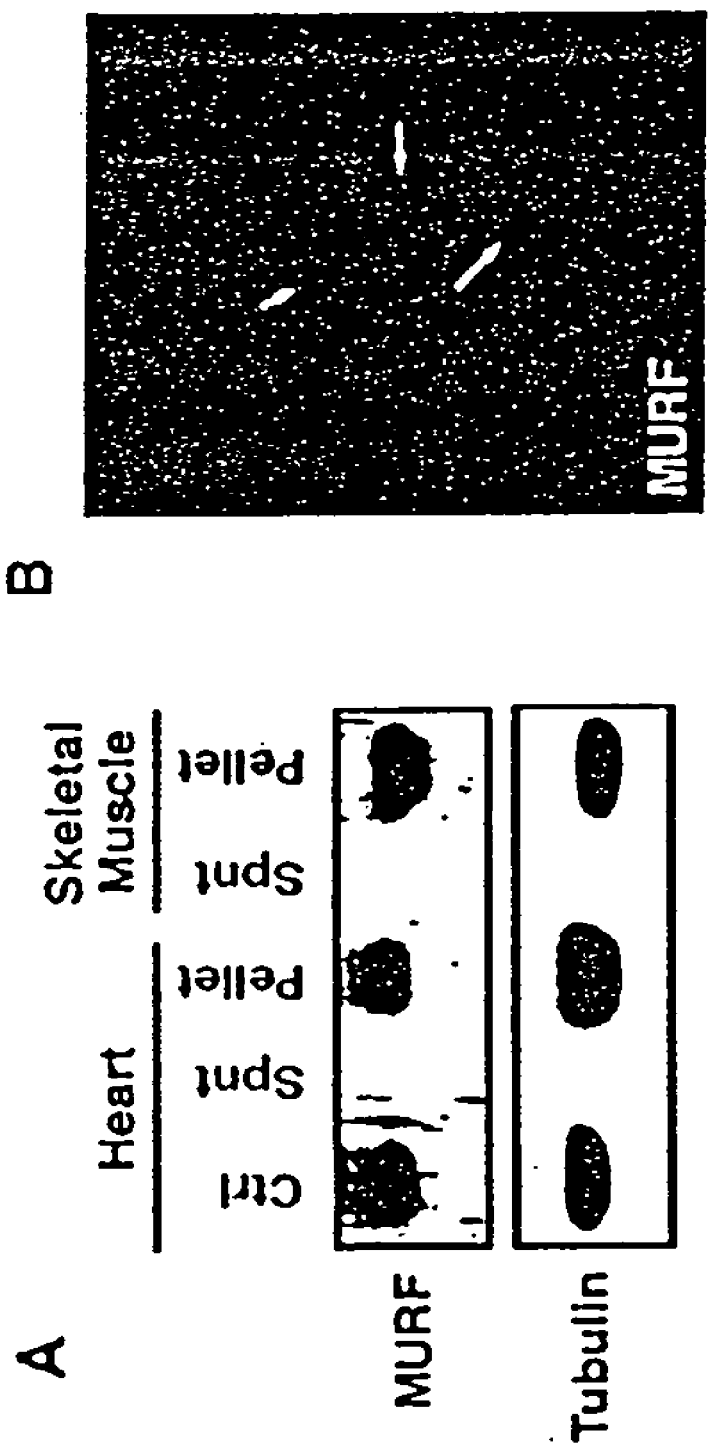
FIGS. 3A–3B—Association of MURF-1 with microtubules demonstrated by microtubule sedimentation assay.

Endogenous MURF-1 cosediments with microtubules from striated muscle. Given the amino acid homology between Mid1 and MURF-1 and the ability of Mid1 to interact with microtubules (Cainarca et al., 1999; Schweiger et al., 1999), the inventors investigated whether MURF-1 was also a microtubule-binding protein. To determine if MURF-1 associates with microtubules, microtubule sedimentation assays were performed using soluble extracts prepared from mouse skeletal muscle and heart. As seen in FIG. 3, MURF-1 was contained in the microtubule pellet from these muscle extracts and was absent from the supernatant, demonstrating a physical association between MURF-1 and microtubules in vivo. No contaminating actin filaments or intermediate filaments were detected in the microtubules pellets under these experimental conditions. Interestingly, a small amount of MURF-1 was also contained in the initial high speed pellet before microtubule polymerization, suggesting its association with structures in addition to microtubules or with cold-stable microtubules that sediment in the initial high speed centrifugation.

Figure 4:
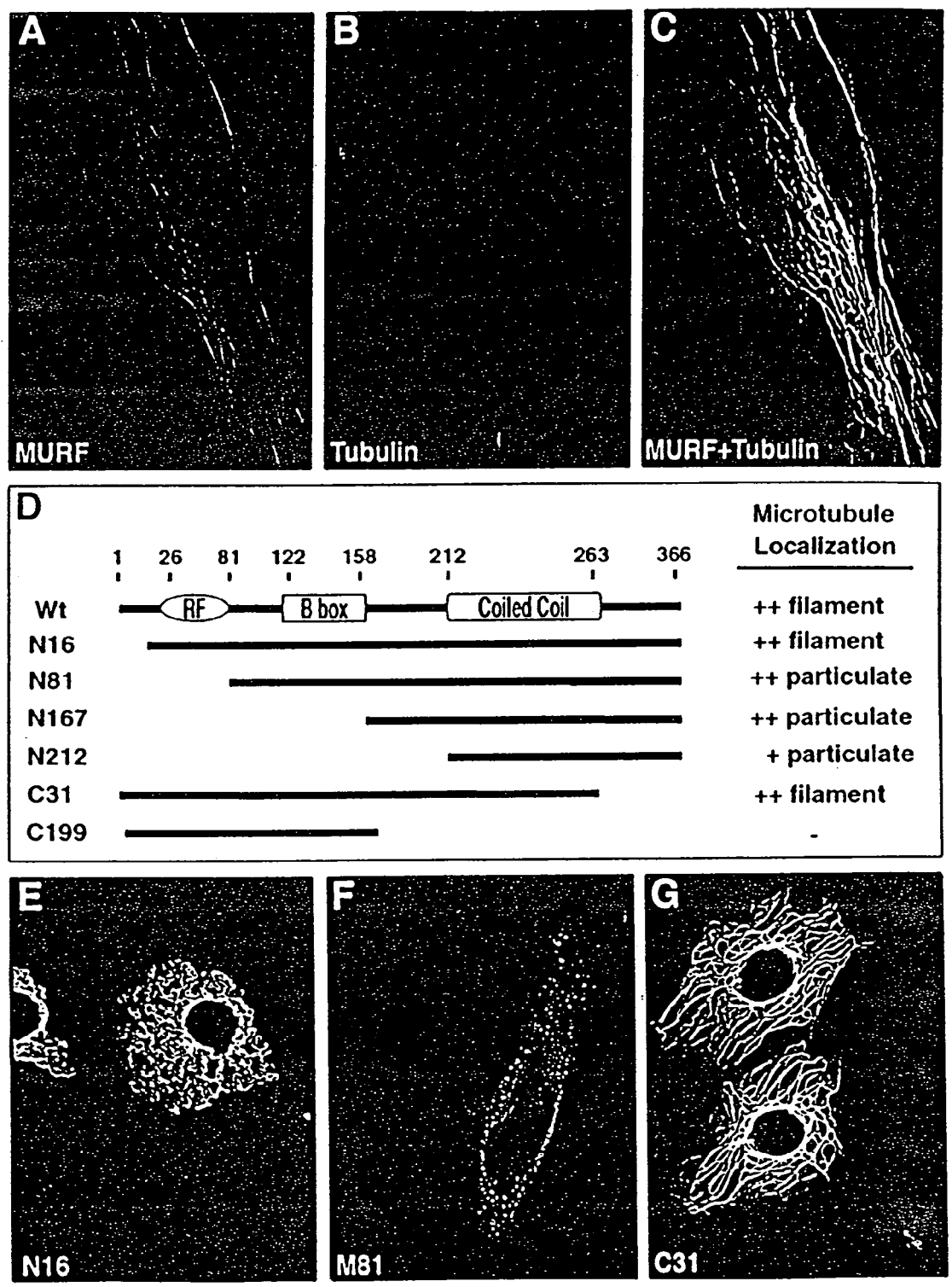
FIGS. 4A–4G—Mapping of domains of MURF-1 required for microtubule localization by immunofluorescence.

Association of MURF-1 with microtubules is mediated by the leucine-rich coiled-coil domain. To identify the domain of MURF-1 required for microtubule association, a series of MURF-1 deletion mutants with myc-tags at their C-termini was constructed and analyzed by immunofluorescence in Hela cells. As seen in FIG. 4A, MURF-1 was incorporated into an undulating reticular network in the cytoplasm, reminiscent of the subcellular distribution of Mid1 and Mid2 (Buchner et al., 1999; Cainarca et al., 1999; Schweiger et al., 1999). This network was extremely stable, remaining intact even after extraction with 1% Triton X-100. The resistance to extraction in high detergent concentrations suggested that MURF-1 associated with a cytoskeletal component.

To determine if MURF-1 colocalized with the cytoskeleton, coimmunofluorescence was performed using antibodies specific to actin, vimentin (intermediate filaments) and tubulin. Microtubules showed the strongest colocalization with MURF-1 (FIGS. 4B and C), in agreement with the results of in vivo microtubule cosedimentation (see FIG. 3). There was no overlap of MURF-1 localization with actin and only partial overlap with intermediate filaments at regions where microtubules and intermediate filaments were in close proximity. Similar localization of MURF-1 to microtubules was observed in skeletal muscle cells (FIG. 3B).

As shown in FIGS. 4D and E, deletion of the 16 amino terminal residues of MURF-1 (mutant N16) did not disrupt colocalization with microtubules. However, the smooth tubular structures formed with full-length MURF-1 were distorted to a thicker and angular structure (FIGS. 4D and E). The significance of this redistribution is unclear. Deletion of amino acids 1–81 (mutant N81), removing the RING-finger domain, also did not abolish microtubule association, but prevented filament formation along microtubules (FIGS. 4D and F and see below). Truncation of MURF-1 to amino acid 167 (mutant N167), deleting the B-box domain, resulted in similar microtubule association without filament formation (FIG. 4D), indicating that the B-box is not involved in microtubule-binding. Deletion of amino acids 1–212 (mutant N212), leaving only the leucine-rich coiled-coil domain and acidic C-terminus, again prevented filament formation without affecting microtubule binding (FIG. 4D). Instead, as observed with mutants N81 and N167, particulate structures were formed that colocalized with microtubules. Deletion of the C-terminal acidic region (mutant C31) did not affect the association of MURF-1 with microtubules nor filament formation (FIGS. 4D and G). Truncation of the acidic and coiled-coil region of MURF (mutant C199), leaving only the RING-finger and B-box domains, produced aggregates that did not colocalize with microtubules (FIG. 4D). Deletion analyses were performed in Cos, 10T1/2, 293 and 3T3 cells with identical results. Taken together, these data demonstrate that the leucine-rich coiled-coil region of MURF-1 is sufficient for colocalization with microtubules, whereas the RING-finger is required for filament formation along microtubules.

Figure 5:
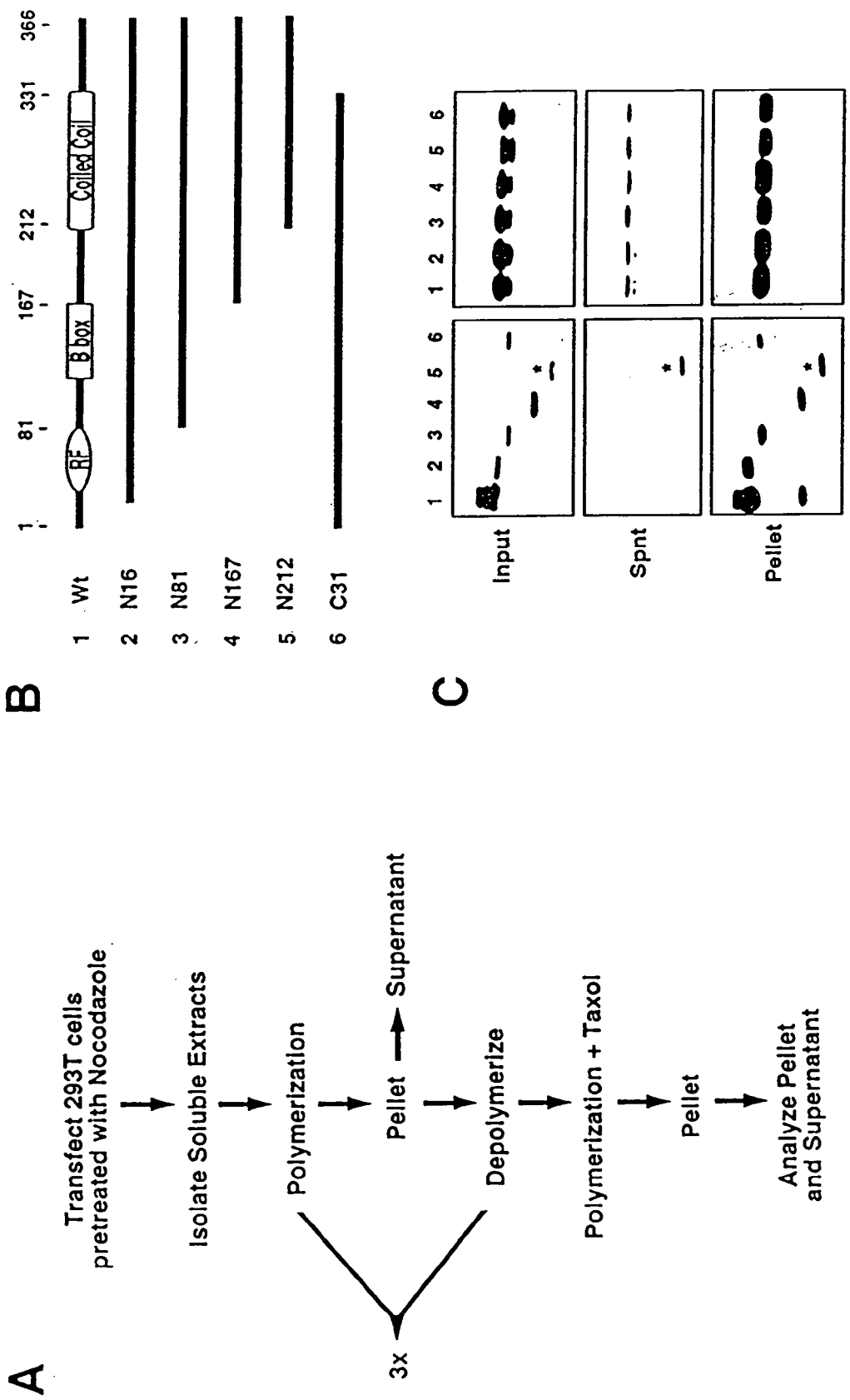
FIGS. 5A–5C—Mapping of domains of MURF-1 required for association with tubulin by cosedimentation.

The leucine-rich coiled-coil domain interacts with microtubules. Given that MURF-1 cosediments with microtubules and the leucine-rich coiled-coil domain is required for colocalization of MURF-1 with microtubules, the inventors determined if this domain also mediates cosedimentation with microtubules 293T fibroblasts were transfected with plasmids expressing wild-type and deletion mutants of MURF-1, simultaneously treated with nocodazole for 24 hours to prevent microtubule association, and soluble extracts prepared. It was necessary to treat cells with nocodazole during transfection due to MURF-1's ability to stabilize microtubules. In experiments not employing simultaneous treatment/transfection, full-length MURF-1, and deletion mutants lacking the N-terminal 16 amino acids (N16) and MURF-1 lacking the C-terminal 31 amino acids (C31), all shown to form filaments along microtubules, were consistently contained exclusively in the initial high speed pellet before microtubule assembly. As seen in FIG. 5C, full-length MURF-1 cosedimented with microtubules in transfected cells. Consistent with the deletion/immunofluorescence analysis (FIG. 4), all MURF-1 deletion mutants containing the leucine-rich coiled-coil domain cosedimented with microtubules. Interestingly, however, mutant N212, which contains only the leucine-rich coiled-coil domain, was also contained in the supernatant after microtubule pelleting (FIG. 5C, lane 5). Since mutant N167 was localized exclusively to the microtubule pellet, this suggests that although the leucine-rich coiled-coil domain is sufficient for association with microtubules, this domain also requires amino acids 167–212 for optimal interaction. Consistent with the aggregation of mutant C199, containing the RING-finger plus B-box, observed by immunofluorescence, this mutant was consistently contained in the initial high speed pellet before microtubule assembly. These data further demonstrate that MURF-1 is capable of cosedimenting with microtubules and that the leucine-rich coiled-coil domain is required for this association.

MURF-1 association with microtubules requires homo-oligomerization mediated by the leucine-rich coiled-coil domain. Coiled-coil domains often mediate protein-protein interactions. To determine if the leucine-rich coiled-coil domain might mediate homo-oligomerization of MURF-1, the inventors performed coimmunoprecipitation experiments using $^{35}$S-labeled in vitro translated myc-tagged MURF-1 and Flag-tagged MURF-1. As summarized in FIG. 6A, MURF-1 was able to self-associate. Deletion of the RING finger, and B-box (mutants N81 and N167) did not affect homo-oligomerization, whereas deletion of the leucine-rich coiled-coil domain abolished homo-oligomerization (mutant C199). These data demonstrate that the leucine-rich coiled-coil domain of MURF-1 is a homo-oligomerization domain. Similarly, the coiled-coil domain of RBCC members XNF7, Rfp, and Cb1 have also been demonstrated to mediate homo-oligomerization (Bartkiewicz et al., 1999; Cao et al., 1997; Li et al., 1994).

Figure 6:
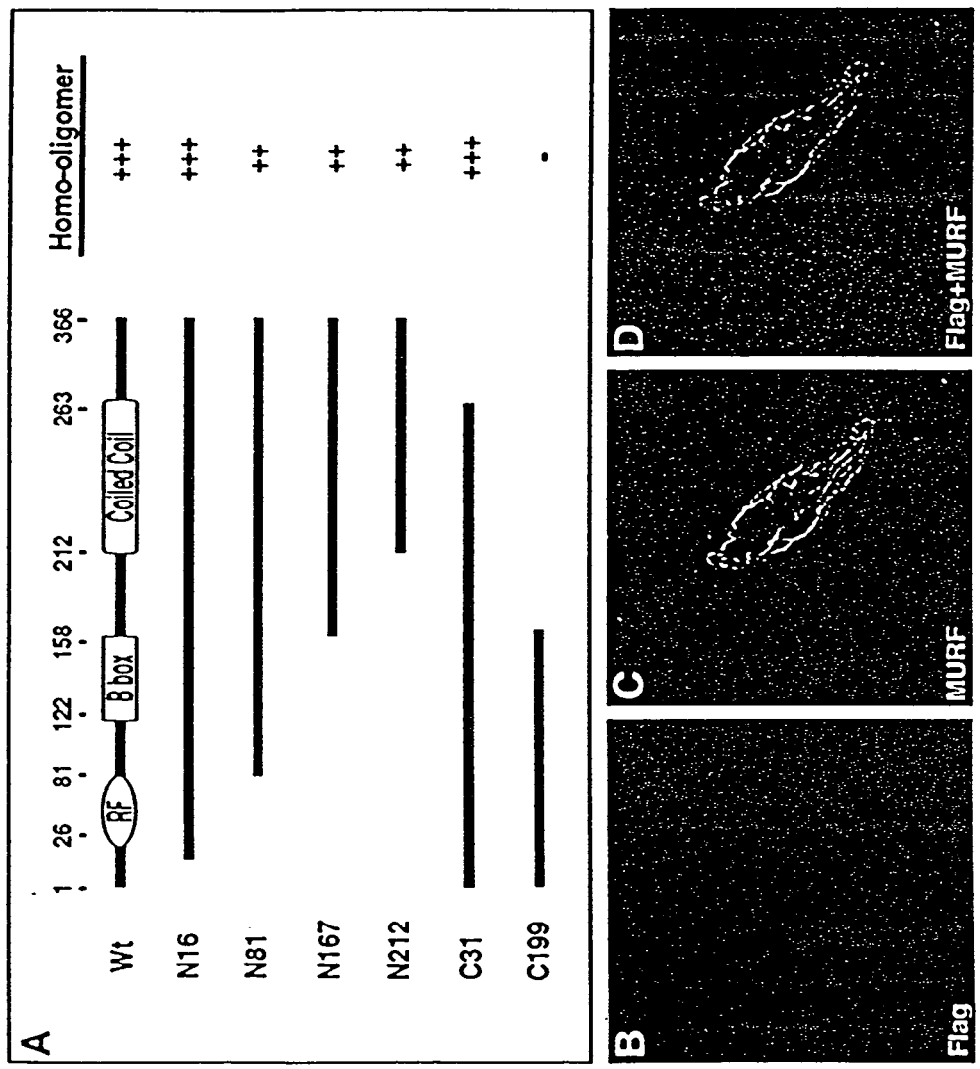
FIGS. 6A–6D—Mapping domains of MURF-1 required for homo-oligomerization.

While constructing epitope-tagged versions of MURF-1, the inventors observed that the Flag-tag placed at the N-terminus of MURF-1 completely inhibited interaction with microtubules, resulting in formation of protein aggregates (see FIG. 6B). Therefore, to determine if MURF-1 associated with microtubules as a homo-oligomer, the N-terminal Flag-tagged MURF and the C-terminal myc-tagged MURF-1 were transfected separately or in combination into Hela cells and immunofluorescence was performed. As seen in FIG. 6B, the Flag-tagged MURF-1 did not significantly colocalize with microtubules, instead forming large aggregates. In contrast, co-expression of Flag-MURF-1 and the C-terminal myc-tagged version resulted in colocalization of both tagged version along the same filamentous structures (FIG. 6D). This demonstrates that MURF-1 associates with microtubules as a homo-oligomer. These data are consistent with the inability of versions of MURF-1 lacking the leucine-rich coiled-coil homo-oligomerization domain to associate with microtubules.

Figure 7:
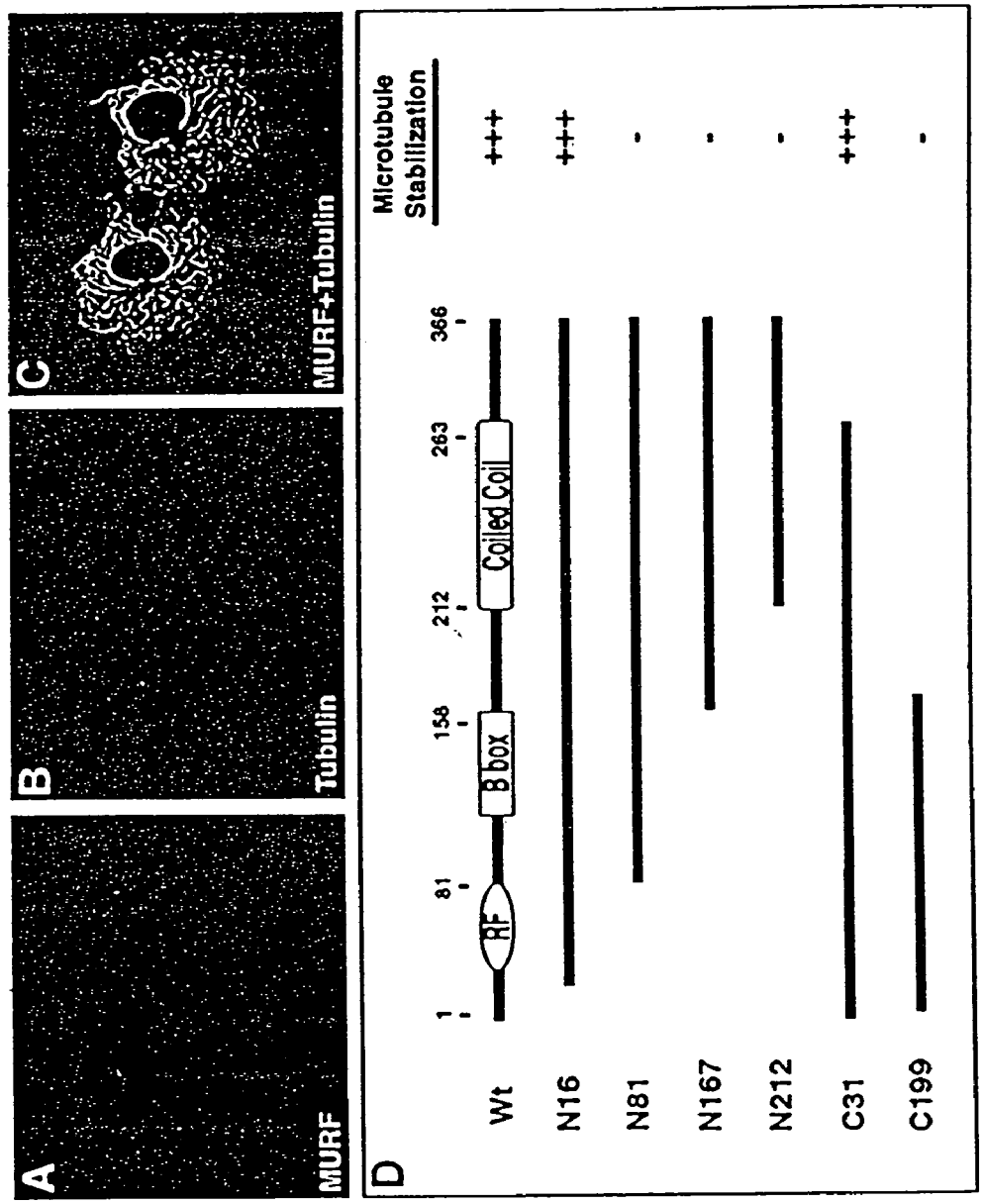
FIGS. 7A–7D—Mapping domains of MURF-1 required for microtubule stabilization.

MURF-1 stabilizes microtubules. Recently, Mid1 was shown to associate with and stabilize microtubules (Cainarca et al., 1999; Spencer et al., 1999). Given the homology of MURF-1 with Mid1 and the ability of endogenous MURF-1 to colocalize and sediment with microtubules, the inventors determined if MURF-1 was able to stabilize microtubules in cultured cells. Cos cells were transfected with MURF-1 expression plasmid, cultured for 2 hours in the presence of 2 µM nocodazole, detergent extracted, and MURF-1 expression was examined by immunofluorescence. As shown in FIGS. 7A–C, MURF-1 prevented depolymerization of microtubules in the presence of nocodazole. In untransfected cells lacking MURF-1, microtubules were completely depolymerized as indicated by the absence of microtubule staining. Similar results were obtained using cold incubation or calcium treatment of detergent-extracted cells to destabilize microtubules.

To identify the domain of MURF-1 required for microtubule stabilization, the previously described deletion mutants of MURF-1 were examined for their ability to protect microtubules from depolymerization in transfected Cos cells. MURF-1 mutants lacking the N-terminal 16 amino acids or the C-terminal 31 amino acids (mutants N16 and C31) were able to protect microtubules from destabilization to a degree comparable to that of full-length MURF (FIG. 7D). Interestingly, deletion mutants of MURF-1 lacking the RING-finger did not stabilize microtubules. This demonstrates that the microtubule stabilizing effects of MURF-1 are dependent on the ability to form filaments along microtubules.

Figure 8:
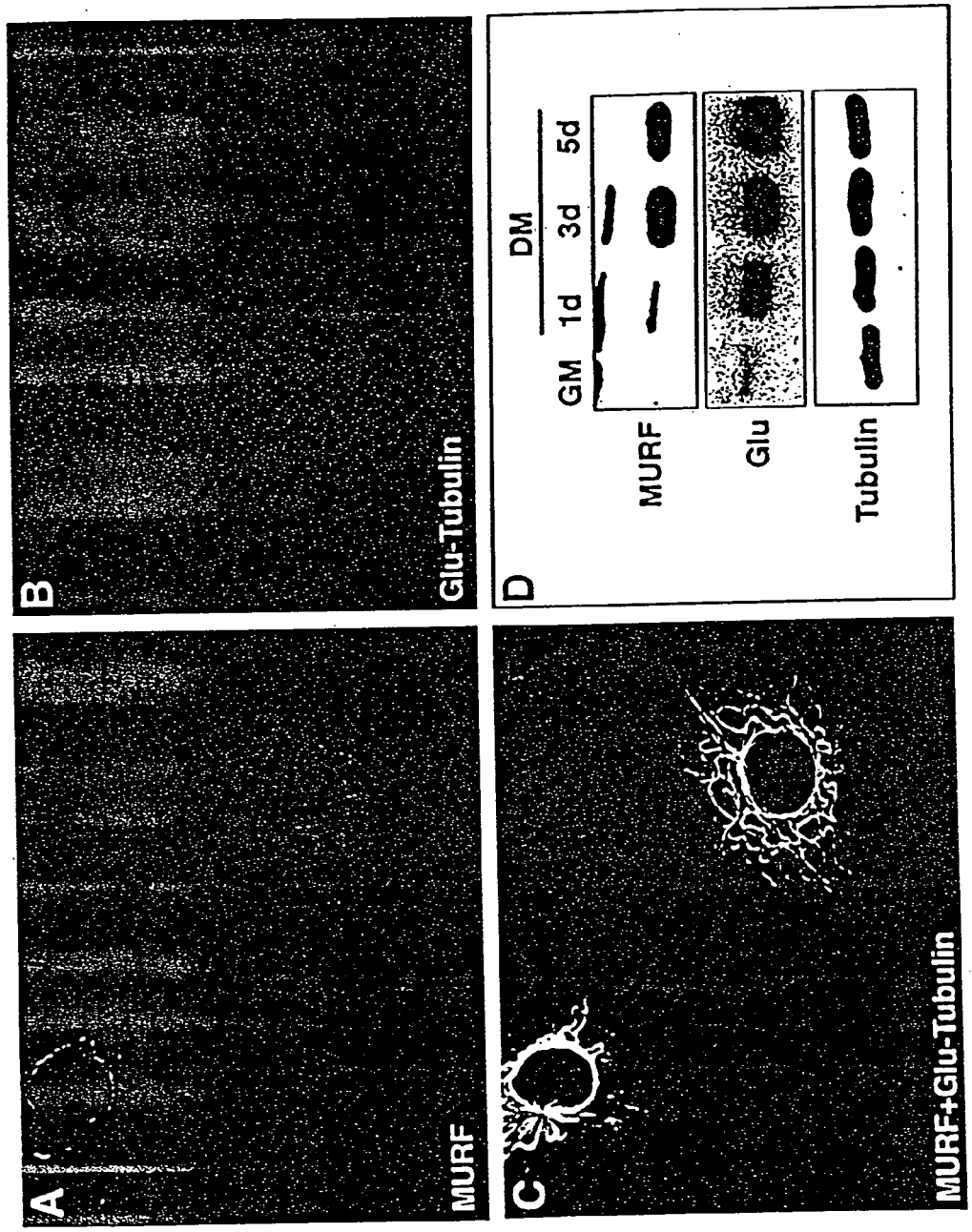
FIGS. 8A–8D—Stabilization of microtubules by MURF-1 in vivo.
Figure 9:
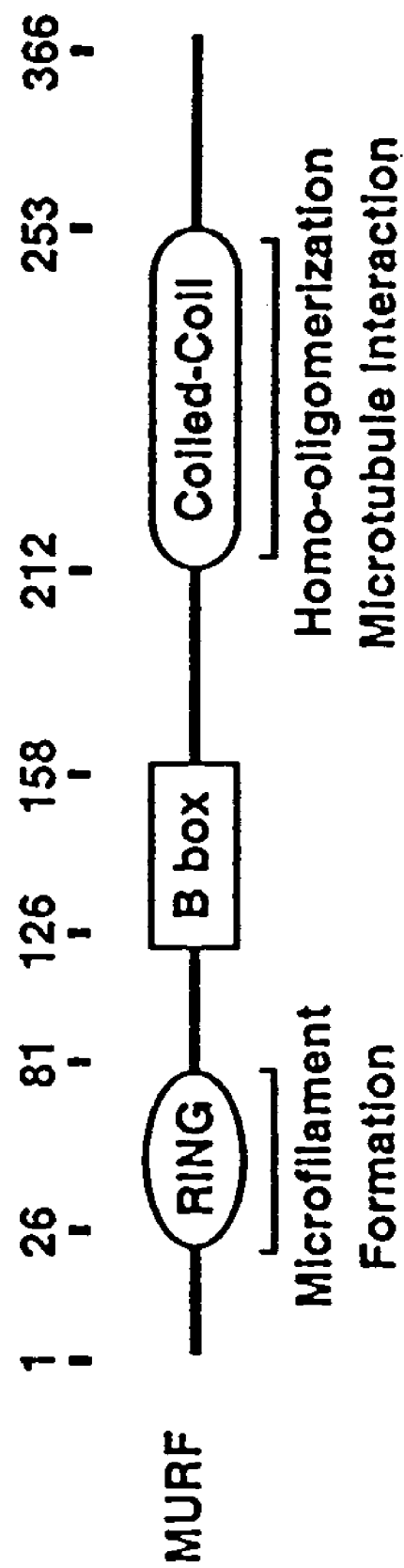
FIG. 9—Functional domain structure of MURF-1. MURF-1 is composed of distinct functional domains. The leucine-rich coiled-coil domain mediates homo-oligomerization and microtubule association. The RING-finger domain is required for filament formation along microtubules.

MURF-1 causes the formation of glutamic acid-modified microtubules. Microtubules exist in several modified forms. The majority of the tubulin contained within microtubules is tyrosinated at its C-terminus. Tubulin that has been detyrosinated can possess a glutamic acid residue at its C-terminus (Glu-tubulin) or this residue can be removed (delta$_2$-tubulin). Tubulin can also be acetylated. Microtubules composed of modified tubulin, such as acetylated tubulin, Glu-tubulin and delta$_2$-tubulin, have been demonstrated to be more stable than unmodified or tyrosinated tubulin. The more stable the microtubule, the longer it exists without depolymerization, and the greater the accumulation of modified tubulin within the microtubule. Therefore, the degree of modification is indicative of the age of the microtubule. As another measure of MURF-1's ability to stabilize microtubules, cells were transfected with MURF-1 and immunostained with antibodies specific to the glutamic acid-modified form of tubulin (Glu-tubulin). As seen in FIG. 8C, only cells possessing the thick tubular network of MURF-1-bound microtubules contain Glu-tubulin, suggesting these microtubules are indeed stable and have existed for a significant period without depolymerization. Identical results were obtained using a delta$_2$-tubulin antibody.

To determine if MURF-1 expression parallels the formation of Glu-modified microtubules during skeletal muscle differentiation, C2 cells were isolated at various stages of differentiation and Glu-tubulin was analyzed by western blot analysis. As seen in FIG. 8D, the appearance of Glu-tubulin mirrors the expression of MURF-1 during muscle differentiation. These data demonstrate that MURF-1/microtubule interaction leads to a dramatic shift in microtubule equilibrium from a dynamic to a static state and suggests a causative role for MURF-1 in the establishment of stable microtubules required for the formation of striated muscle.

Tissue expression of MURF2 and MURF3 in embryonic and adults. As with MURF1, the inventors determined the localization of expression of MURF2 and MURF3 in in situ fluorescence studies. Like MURF1, MURF2 appears to be expressed primarily in heart tissue, but also in skeletal muscle. Heart expression appears at about E10.5 and increases at E12.5 and E16.5. MURF3, in contrast, appears to be expressed selectively in cardiac tissue, although like MURF1 and MURF2, its expression increases throughout embryogensis.

MURFs are intermediate filament binders. Using antibodies to MURFs and to intermediate filaments such as desmin, vimentin and cytokeratin, the inventors determined that each of MURF1, MURF2 and MURF3 associated with intermediate filaments, indicating a role for MURFs in the stabilization of these molecules as well. In addition, MURF1 was shown to localize to Z-lines of cultured cardiomyocytes, and MURF3 localized to Z-lines and the nucleus.

All of the COMPOSITIONS and METHODS disclosed and claimed herein can be made and executed without undue experimentation in light of the present disclosure. While the compositions and methods of this invention have been described in terms of preferred embodiments, it will be apparent to those of skill in the art that variations may be applied to the COMPOSITIONS and METHODS and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

IX. References

The following references, to the extent that they provide exemplary procedural or other details supplementary to those set forth herein, are specifically incorporated herein by reference.

Angel et al., *Mol. Cell. Biol.*, 7:2256, 1987a.
Angel et al., *Cell*, 49:729, 1987b.
Antin, Forry-Schaudies, Friedman, Tapscott, Holtzer, "Taxol induces postmitotic myoblasts to assemble interdigitating microtubule-myosin arrays that exclude actin filaments," *J. Cell Biol.*, 90(2):300–8 (1981)
Baichwal and Sugden, "Vectors for gene transfer derived from animal DNA viruses: Transient and stable expression of transferred genes", In: *Gene Transfer*, Kucherlapati R, ed., New York, Plenum Press, pp. 117–148, 1986.
Banerji et al., *Cell*, 35:729, 1983.
Barany and Merrifield, The Peptides, Gross and Meienhofer, eds., Academic Press, New York, pp. 1–284, 1979.
Bartkiewicz, Houghton, Baron, "Leucine zipper-mediated homodimerization of the adaptor protein c-Cb1. A role in c-Cb1's tyrosine phosphorylation and its association with epidermal growth factor receptor," *J. Biol. Chem.*, 274 (43):30887–95, 1999.
Benjamin, Shelton, Garry, Richardson, "Temporospatial expression of the small HSP/alpha B-crystallin in cardiac and skeletal muscle during mouse development," *Dev. Dyn.*, 208(1):75–84, 1997.
Benvenisty and Neshif, "Direction introduction of genes into rats and expression of the genes", *Proc. Nat'l Acad. Sci. USA*, 83:9551–9555, 1986.
Berkhout et al., *Cell*, 59:273, 1989.
Blanar et al., *EMBO J.*, 8:1139, 1989.
Bodine and Ley, *EMBO J.*, 6:2997, 1987.
Borden, "RING fingers and B-boxes: zinc-binding protein-protein interaction domains," *Biochem. Cell Biol.*, 76:351–358, 1998.
Boshart et al., *Cell*, 41:521, 1985.
Bosze et al., *EMBO J.*, 5:1615, 1986.
Braddock et al., *Cell*, 58:269, 1989.
Brinster et al., *Proc. Nat'l Acad. Sci. USA*, 82: 4438–4442, 1985.
Buchner, Montini, Andolfi, Quaderi, Cainarca, Messali, Bassi, Ballabio, Meroni, Franco, "MID2, a homologue of the Opitz syndrome gene MID1: similarities in subcellular localization and differences in expression during development," *Hum. Mol. Genet.*, 8:1397–1407, 1999.
Bulla and Siddiqui, *J. Virol.*, 62:1437, 1986.
Cainarca, Messali, Ballabio, Meroni, "Functional characterization of the Opitz syndrome product (midin): evidence for homodimerization and association with microtubules throughout the cell cycle," *Hum. Mol. Genet.*, 8:1387–1396, 1999.
Campbell, In: *Monoclonal Antibody Technology, Laboratory Techniques in Biochemistry and Molecular Biology*, Vol. 13, Burden and Von Knippenberg, Eds. pp. 75–83, Amsterdam, Elseview, 1984.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Cao, Borden, Freemont, Etkin, "Involvement of the rfp tripartite motif in protein-protein interactions and subcellular distribution," *J. Cell Sci.*, 110 ( Pt 14): 1563–71, 1997.
Capaldi et al., *Biochem. Biophys. Res. Comm.*, 76:425, 1977
Celander and Haseltine, *J. Virology*, 61:269, 1987.
Celander et al., *J. Virology*, 62:1314, 1988.
Chandler et al., *Cell*, 33:489, 1983.
Chang et al., "Foreign gene delivery and expression in hepatocytes using a hepatitis B virus vector", *Hepatology*, 14:124A, 1991.
Chang et al., *Mol. Cell. Biol.*, 9:2153, 1989.
Chatterjee et al., *Proc. Nat'l Acad. Sci. USA.*, 86:9114, 1989.

Chen and Okayama, "High-efficiency transfection of mammalian cells by plasmid DNA", *Mol. Cell Biol.,* 7:2745–2752, 1987.

Choi et al., *Cell,* 53:519, 1988.

Coffin, Retroviridae and Their Replication. In: *Virology,* Fields et al., eds., Raven Press, New York, pp. 1437–1500, 1990.

Cohen et al., "A repetitive sequence element 3' of the human c-Ha-ras1 gene has enhancer activity", *J. Cell. Physiol.,* 5:75, 1987

Cook et al., "In vitro splicing of the ribosomal RNA precursor of Tetrahymena: involvement of a guanosine nucleotide in the excision of the intervening sequence," *Cell,* 27:487–496, 1981.

Costa et al., *Mol. Cell. Biol.,* 8:81, 1988.

Couch et al., "Immunization with types 4 and 7 adenovirus by selective infection of the intestinal tract," *Am. Rev. Resp. Dis.,* 88:394–403, 1963.

Coupar et al., "A general method for the construction of recombinant vaccinia virus expressing multiple foreign genes", *Gene,* 68:1–10, 1988.

Cripe et al., *EMBO J.,* 6:3745, 1987.

Culotta and Hamer, *Mol. Cell. Biol.,* 9:1376, 1989.

Dandolo et al., *J. Virology,* 47:55, 1983.

De The, Lavau, Marchio, Chomienne, Degos, Dejean, "The PML-RARα fusion mRNA generated by the t(15,17) translocation in acute promyelocytic leukemia encodes a functionally altered RAR," *Cell,* 66(4):675–684, 1991.

De Villiers et al., *Nature,* 312:242, 1984.

Deschamps et al., *Science,* 230:1174, 1985.

Dubensky et al., "Direct transfection of viral and plasmid DNA into the liver or spleen of mice", *Proc. Nat'l Acad. Sci. USA,* 81:7529–7533, 1984.

Dunning, "Prostate cancer in the rat," *Natl Cancer Inst Monogr* 12:351–369, 1963.

Edbrooke et al., *Mol. Cell. Biol.,* 9:1908, 1989.

Edlund et al., *Science,* 230:912, 1985.

Fechheimer et al., "Transfection of mammalian cells with plasmid DNA by scrape loading and sonication loading", *Proc. Nat'l Acad. Sci. USA,* 84:8463–8467, 1987.

Feng and Holland, *Nature,* 334:6178, 1988.

Ferkol et al., "Regulation of the phosphoenolpyruvate carboxykinase/human factor IX gene introduced into the livers of adult rats by receptor-mediated gene transfer", *FASEB J.,* 7:1081–1091, 1993.

Firak and Subramanian, *Mol. Cell. Biol.,* 6:3667, 1986.

Forster & Symons, "Self-cleavage of plus and minus RNAs of a virusoid and a structural model for the active sites," *Cell,* 49:211–220, 1987.

Fraley et al., "Entrapment of a bacterial plasmid in phospholipid vesicles: Potential for gene transfer", *Proc. Nat'l Acad. Sci. USA,* 76:3348–3352, 1979.

Freifelder, *Physical Biochemistry Applications to Biochemistry and Molecular Biology,* 2nd ed. Wm. Freeman and Co., New York, N.Y., 1982.

Friedmann, "Progress toward human gene therapy", *Science,* 244:1275–1281, 1989.

Gefter et al., *Somatic Cell Genet.,* 3: 231–236, 1977.

Gerlach et al., "Construction of a plant disease resistance gene from the satellite RNA of tobacco rinspot virus," *Nature (London),* 328:802–805, 1987.

Ghosh and Bachhawat, Targeting of Liposomes to Hepatocytes. In: *Liver Diseases, Targeted Diagnosis and Therapy Using Specific Receptors and Ligands.* Wu et al., eds., Marcel Dekker, New York, pp. 87–104, 1991.

Ghosh-Choudhury et al., *EMBO J.,* 6:1733–1739, 1987.

Gleeson, Lin, Flanagan, Walsh, "Doublecortin is a microtubule-associated protein, and is expressed widely by migrating neurons," *Neuron.,* 2:257–271, 1999.

Gloss et al., *EMBO J.,* 6:3735, 1987.

Godbout et al., *Mol. Cell. Biol.,* 8:1169, 1988.

Goding, 1986, In: *Monoclonal Antibodies: Principles and Practice,* 2d ed., Academic Press, Orlando, Fla., pp. 60–61, and 71–74, 1986.

Gomez-Foix et al., *J. Biol. Chem.,* 267:25129–25134, 1992.

Gopal, "Gene transfer method for transient gene expression, stable transfection, and cotransfection of suspension cell cultures", *Mol. Cell Biol.,* 5:1188–1190, 1985.

Graham and Prevec, In: *Methods in Molecular Biology: Gene Transfer and Expression Protocol,* E. J. Murray, ed., Humana Press, Clifton, N.J., 7:109–128, 1991.

Graham and van der Eb, "A new technique for the assay of infectivity of human adenovirus 5 DNA", *Virology,* 52:456–467, 1973.

Graham et al., "Characteristics of a human cell line transformed by DNA from human adenovirus type 5 ", *J. Gen. Virol.,* 36:59–72, 1977.

Grunhaus and Horwitz, "Adenovirus as cloning vector", *Seminar in Virology,* 3:237–252, 1992.

Gunderson, Khawaja, Bulinski, "Generation of stable, post-translationally modified microtubule array is an early event in myogenic differentiation," *J. Cell Biol.,* 109:2275–2288, 1989.

Harland and Weintraub, "Translation of mammalian mRNA injected into *Xenopus oocytes* is specifically inhibited by antisense RNA", *J. Cell Biol.,* 101:1094–1099, 1985.

Harlow and Lane, Antibodies: A Laboratory manual, Cold Spring Harbor Laboratory, 1988.

Haslinger and Karin, *Proc. Nat'l Acad. Sci. USA.,* 82:8572, 1985.

Hauber and Cullen, *J. Virology,* 62:673, 1988.

Hen et al., *Nature,* 321:249, 1986.

Hensel et al., *Lymphokine Res.,* 8:347, 1989.

Hermonat and Muzycska, "Use of adenoassociated virus as a mammalian DNA cloning vector: Transduction of neomycin resistance into mammalian tissue culture cells", *Proc. Nat. Acad. Sci. USA,* 81:6466–6470, 1984.

Herr and Clarke, *Cell,* 45:461, 1986.

Hersdorffer et al., *DNA Cell Biol.,* 9:713–723, 1990.

Herz and Gerard, *Proc. Nat'l Acad. Sci. USA,* 90:2812–2816, 1993.

Hirochika et al., *J. Virol.,* 61:2599, 1987.

Hirsch et al., *Mol. Cell. Biol,* 10:1959, 1990.

Horlick and Benfield, *Mol. Cell. Biol.,* 9:2396, 1989.

Horwich, et al., "Synthesis of hepadnavirus particles that contain replication-defective duck hepatitis B virus genomes in cultured HuH7 cells", *J. Virol.,* 64:642–650, 1990.

Hsieh, Liu, Kostas, Chang, Sternberg, Fire, "The RING finger/B-Box factor TAM-1 and a retinoblastoma-like protein LIN-35 modulate context-dependent gene silencing in Caenorhabditis elegans," *Genes Dev.,* 13(22):2958–2970, 1999.

Huang et al., *Cell,* 27:245, 1981.

Hwang et al., *Mol. Cell. Biol.,* 10:585, 1990.

Imagawa et al., *Cell,* 51:251, 1987.

Imbra and Karin, *Nature,* 323:555, 1986.

Imperiale and Nevins, *Mol. Cell. Biol.,* 4:875, 1984.

Innis et al., *PCR Protocols,* Academic Press, Inc., San Diego Calif., 1990.

Jakobovits et al., *Mol. Cell. Biol.,* 8:2555, 1988.

Jameel and Siddiqui, *Mol. Cell. Biol.,* 6:710, 1986.

Jaynes et al., *Mol. Cell. Biol.,* 8:62, 1988.

Johnson et al., *Mol. Cell. Biol.*, 9:3393, 1989.
Johnson et al., Peptide Turn Mimetics" IN: *Biotechnology And Pharmacy*, Pezzuto et al., eds., Chapman and Hall, New York, 1993.
Jones and Shenk, *Cell*, 13:181–188, 1978.
Joyce, "RNA evolution and the origins of life," *Nature*, 338:217–244, 1989.
Kadesch and Berg, *Mol. Cell. Biol.*, 6:2593, 1986.
Kaech, Ludin, Matus, "Cytoskeletal plasticity in cells expressing neuronal microtubule-associated proteins," *Neuron*, 17(6):1189–99, 1996.
Kaneda et al., "Increased expression of DNA cointroduced with nuclear protein in adult rat liver", *Science*, 243:375–378, 1989.
Karin et al., *Mol. Cell Biol.*, 7:606, 1987.
Karlsson et al., *EMBO J.*, 5:2377–2385, 1986.
Katinka et al., *Cell*, 20:393, 1980.
Katinka et al., *Nature*, 290:720, 1981.
Kato et al., "Expression of hepatitis B virus surface antigen in adult rat liver", *J. Biol. Chem.*, 266:3361–3364, 1991.
Kaufmann, Kirsch, Irintchev, Wernig, Starzinski-Powitz, "The M-cadherin catenin complex interacts with microtubules in skeletal muscle cells: implications for the fusion of myoblasts," *J. Cell Sci.*, 112:55–67, 1999.
Kawamoto et al., *Mol. Cell. Biol.*, 8:267, 1988.
Kim & Cook, "Three dimensional model of the active site of the self-splicing rRNA precursor or Tetrahymena," *Proc. Nat'l Acad. Sci. USA*, 84:8788–8792, 1987.
Klamut et al., *Mol. Cell. Biol.*, 10:193, 1990.
Klein et al., "High-velocity microprojectiles for delivering nucleic acids into living cells", *Nature*, 327:70–73, 1987.
Koch et al., *Mol. Cell. Biol.*, 9:303, 1989.
Kohler and Milstein, *Eur. J. Immunol.*, 6:511–519, 1976.
Kohler and Milstein, *Nature*, 256:495497, 1975.
Kosik, "Tau protein and neurodegenration," *Mol. Neurobiol.*, 4(34):171–179, 1990.
Koulakoff, Boucher, Chafey, Schaar, Vinet, Friocourti, McDonnell, Reiner, Kahn, McConnell, Berwald-Netter, Denoulet, Chelly, "Doublecortin is a developmentally regulated, microtubule-associated protein expressed in migrating and differentiating neurons," *Neuron*, 2:247–256, 1999.
Kriegler and Botchan, In: *Eukaryotic Viral Vectors*, Y. Gluzman, ed., Cold Spring Harbor: Cold Spring Harbor Laboratory, N.Y., 1982.
Kriegler et al., In: *Gene Expression*, D. Hamer and M. Rosenberg, eds., New York: Alan R. Liss, 1983.
Kriegler et al., *Cell*, 38:483, 1984a.
Kriegler et al., In: *Cancer Cells 2/Oncogenes and Viral Genes*, Van de Woude et al. eds, Cold Spring Harbor, Cold Spring Harbor Laboratory, 1984b.
Kriegler et al., *Cell*, 53:45, 1988.
Kriegler and Botchan, *Mol. Cell. Biol.*, 3:325, 1983.
Kuhl et al., *Cell*, 50:1057, 1987.
Kunz et al., *Nucl. Acids Res.*, 17:1121, 1989.
Kyte and Doolittle, *J. Mol. Biol.*, 157(1):105–132, 1982.
Larsen et al., *Proc. Nat'l Acad. Sci. USA*, 83:8283, 1986.
LaPointe, Wu, Greenberg, Gardner, "Upstream sequences confer atrial-specific expression on the human atrial natriuretic factor gene." *J. Biol. Chem.*, 263(19):9075–8, 1988.
Laspia et al., *Cell*, 59:283, 1989.
Latimer et al., *Mol. Cell. Biol.*, 10:760, 1990.
Le Gal La Salle et al., *Science*, 259:988–990, 1993.
Lee et al., *Nature*, 294:228, 1981.
Levinson et al., *Nature*, 295:79, 1982.
Levrero et al., *Gene*, 101: 195–202, 1991.
Li, Shou, Kloc, Reddy, Etkin, "The association of *Xenopus* nuclear factor 7 with subcellular structures is dependent upon phosphorylation and specific domains," *Exp. Cell Res.*, 13(2):473–81, 1994.
Lo, Nigro, Chong, Smith, Dobyns, Carrozzo, Ledbetter, "Point mutations and an intragenic deletion in LIS1, the lissencephaly causative gene in isolated lissencephaly sequence and Miller-Dieker syndrome," *Hum. Mol. Genet.*, 6(2):157–64, 1999.
Lusky et al., *Mol. Cell. Biol.*, 3:1108, 1983.
Lusky and Botchan, *Proc. Nat'l Acad. Sci. USA*, 83:3609, 1986.
Macejak and Sarnow, *Nature*, 353:90–94, 1991.
Majors and Varmus, *Proc. Nat'l Acad. Sci. USA*, 80:5866, 1983.
Mangan and Olmsted, "A muscle-specific variant of the microtubule-associated protein 4 (MAP4) is required for myogenesis," *Dev.* 122:771–781, 1996.
Manipulating the Mouse Embryo: A Laboratory Manual, 2nd ed., Hogan et al., eds., Cold Spring Harbor Laboratory Press, 1994.
Mann et al., "Construction of a retrovirus packaging mutant and its use to produce helper-free defective retrovirus", *Cell*, 33:153–159, 1983.
Markowitz et al., *J. Virol.*, 62:1120–1124, 1988.
Marszalek, Ruiz-Lozano, Roberts, Chien, Goldstein, "Situs inversus and embryonic ciliary morphogenesis defects in mouse mutants lacking the KIF3A subunit of kinesin-II," *Proc. Nat'l Acad. Sci.*, 96(9):5043–5048, 1999.
McNeall et al., *Gene*, 76:81, 1989.
Merrifield, *Science*, 232: 341–347, 1986.
Michel & Westhof, "Modeling of the three-dimensional architecture of group I catalytic introns based on comparative sequence analysis," *J. Mol. Biol.*, 216:585–610, 1990.
Miksicek et al., *Cell*, 46:203, 1986.
Mordacq and Linzer, *Genes and Dev.*, 3:760, 1989.
Moreau et al., *Nucl. Acids Res.*, 9:6047, 1981.
Muesing et al., *Cell*, 48:691, 1987.
Mulligan, *Science*, 260:926–932, 1993.
Myers, EP 0273085
Nguyen, Chari, Gruber, Lue, Chapin, Bulinski, "Overexpression of full- or partial-length MAP4 stabilizes microtubules and alters cell growth," *J. Cell Sci.*, 110 (Pt2): 281–94, 1997.
Nguyen, Gruber, McGraw, Sheetz, Bulinski, "Stabilization and functional modulation of microtubules by microtubule-associated protein 4," *Biol. Bull.*, 194(3):354–357, 1998.
Nicolas and Rubinstein, In: *Vectors: A survey of molecular cloning vectors and their uses*, Rodriguez and Denhardt, eds., Stoneham: Butterworth, pp. 494–513, 1988.
Nicolau and Sene, "Liposome-mediated DNA transfer in eukaryotic cells", *Biochim. Biophys. Acta*, 721:185–190, 1982.
Nicolau et al., "Liposomes as carriers for in vivo gene transfer and expression," *Methods Enzymol.*, 149:157–176, 1987.
Ondek et al., *EMBO J.*, 6:1017, 1987.
Ornitz et al., *Mol. Cell. Biol.*, 7:3466, 1987.
Palmiter et al., *Nature*, 300:611, 1982.
Paskind et al., "Dependence of moloney murine leukemia virus production on cell growth", *Virology*, 67:242–248, 1975.
Pech et al., *Mol. Cell. Biol.*, 9:396, 1989.
Pelletier and Sonenberg, *Nature*, 334:320–325, 1988.

Perales et al., "Gene transfer in vivo: Sustained expression and regulation of genes introduced into the liver by receptor-targeted uptake", *Proc. Nat'l Acad. Sci.* 91:4086–4090, 1994.

Perez-Stable and Constantini, *Mol. Cell. Biol.*, 10: 1116, 1990.

Pignon et al., *Hum. Mutat.*, 3: 126–132, 1994.

Pinkert et al., *Genes and Dev.*, 1:268, 1987.

Ponta et al., *Proc. Nat'l Acad. Sci. USA.*, 82:1020, 1985.

Potter et al., "Enhancer-dependent expression of human k immunoglobulin genes introduced into mouse pre-B lymphocytes by electroporation," *Proc. Nat'l Acad. Sci. USA*, 81:7161–7165, 1984.

Quaderi, Schweiger, Gaudenz, Franco, Rugarli, Berger, Feldman, Volta, Andolfi, Gilgenkrantz, Marion, Hennekam, Opitz, Muenke, Ropers, Ballabio, "Opitz G/BBB syndrome, a defect in midline development, is due to mutation in a new RING finger gene on Xp22," *Nat. Gen.*, 17:285–291, 1997.

Quinn et al., *Mol. Cell. Biol.*, 9:4713, 1989.

Racher et al., *Biotechnology Techniques*, 9:169–174, 1995.

Ragot et al., *Nature*, 361:647–650, 1993.

Rawls, Valdez, Zhang, Richardson, Klein, Olson, "Overlapping functions of the myogenic bHLH genes MRF4 and MyoD revealed in double mutant mice," *Development*, 125(13):2349–2358, 1998.

Reinhold-Hurek & Shub, "Self-splicing introns in tRNA genes of widely divergent bacteria," *Nature*, 357:173–176, 1992.

Reisman and Rotter, *Mol. Cell. Biol.*, 9:3571, 1989.

Renan, "Cancer genes: Current status, future prospects and applications in radiotherapy/oncology," *Radiother. Oncol.*, 19:197–218, 1990.

Resendez Jr. et al., *Mol. Cell. Biol.*, 8:4579, 1988.

Rich et al., *Hum. Gene Ther.*, 4:461476, 1993.

Ridgeway, Mammalian Expression Vectors, In: *Vectors: A Survey of Molecular Cloning Vectors and Their Uses*, Rodriguez et al., eds., Stoneham: Butterworth, pp. 467–492, 1988.

Ripe et al., *Mol. Cell. Biol.*, 9:2224, 1989.

Rippe et al., "DNA-mediated gene transfer into adult rat hepatocytes in primary culture," *Mol. Cell. Biol.*, 10:689–695, 1990.

Rittling et al., *Nucl. Acids Res.*, 17:1619, 1989.

Rosen et al., *Cell*, 41:813, 1988.

Rosenfeld et al., In vivo transfer of the human cystic fibrosis transmembrane conductance regulator gene to the airway epithelium. *Cell*, 68:143–155, 1992.

Rosenfeld et al., *Science*, 252:431–434, 1991.

Roux et al., "A versatile and potentially general approach to the targeting of specific cell types by retroviruses: Application to the infection of human cells by means of major histocompatibility complex class I and class II antigens by mouse ecotropic murine leukemia virus-derived viruses", *Proc. Nat'l Acad. Sci. USA*, 86:9079–9083, 1989.

Sakai et al., *Genes and Dev.*, 2:1144, 1988.

Sambrook et al., In: *Molecular Cloning: A Laboratory Manual*, 2d Ed., Cold Spring Harbor Laboratory Press, Cold Spring Harbor, N.Y., 1989.

Samulski et al., *J. Virol.*, 61(10):3096–3101, 1987.

Sapir, Cahana, Seger, Nekhai, Reiner, "LIS1 is a microtubule-associated phosphoprotein," Eur. J. Biochem., 265(1):181–8., 1999

Sapir, Elbaum, Reiner, "Reduction of microtubule catastrophe events by LIS1, platelet-activating factor acetylhydrolase subunit," *EMBO J.*, 16(23):6977–8694, 1997.

Sarver, et al., "Ribozymes as potential anti-HIV-1 therapeutic agents," *Science*, 247:1222–1225, 1990.

Satake et al., *J. Virology*, 62:970, 1988.

Sato, Nagai, Kuppuswamy, Narishige, Koide, Menick, Cooper, "Micortubule stabilization in pressure overload cardiac hypertrophy," *J. Cell Biol.*, 4:963–973, 1997.

Saurin, Borden, Boddy, Freemont, "Does this have a familiar RING? TIBS. June: 208–214, 1996.

Scanlon et al., "Ribozyme-mediated cleavages of c-fos mRNA reduce gene expression of DNA synthesis enzymes and metallothionein," *Proc. Nat'l Acad. Sci. USA*, 88:10591–10595, 1991.

Schaffner et al., *J. Mol. Biol.*, 201:81, 1988.

Schweiger, Foerster, Lehmann, Suckow, Muller, Walter, Davies, Porter, van Bokhoven, Lunt, Traub, Ropers, "The Opitz syndrome gene product, MID1, associates with microtubules," *Proc. Nat'l Acad. Sci. USA*, 96:2794–2799, 1999.

Searle et al., *Mol. Cell. Biol.*, 5:1480, 1985.

Sharp and Marciniak, *Cell*, 59:229, 1989.

Shaul and Ben-Levy, *EMBO J.*, 6:1913, 1987.

Sherman et al., *Mol. Cell. Biol.*, 9:50, 1989.

Sleigh and Lockett, *J. EMBO*, 4:3831, 1985.

Spalholz et al., *Cell*, 42:183, 1985.

Spandau and Lee, *J. Virology*, 62:427, 1988.

Spandidos and Wilkie, *EMBO J.*, 2:1193, 1983.

Spencer and Misra, "Expression of the serum response factor gene is regulated by serum response factor binding sites," *J. Biol. Chem.*, 271(28): 16535–43, 1996.

Spencer, Baron, Olson, "Cooperative transcriptional activation by serum response factor and the high mobility group protein SSRP1," *J. Biol. Chem.*, 274(22):15686–93, 1999.

Stephens and Hentschel, *Biochem. J.*, 248:1, 1987.

Stewart and Young, Solid Phase Peptide Synthesis, 2d. ed., Pierce Chemical Co., 1984.

Stratford-Perricaudet and Perricaudet, Gene transfer into animals: the promise of adenovirus. In: *Human Gene Transfer*, O. Cohen-Haguenauer et al., eds., John Libbey Eurotext, France, pp. 51–61, 1991.

Stratford-Perricaudet et al., "Evaluation of the transfer and expression in mice of an enzyme-encoding gene using a human adenovirus vector", *Hum. Gene. Ther.*, 1:241–256, 1990.

Stuart et al., *Nature*, 317:828, 1985.

Supp, Brueckner, Kuehn, Witte, Lowe, McGrath, Corrales, Potter, "Targeted deletion of the ATP binding domain of left-right dynein confirms its role in specifying development of left-right asymmetries," *Dev.*, 126:5495–5504, 1999.

Swartzendruber and Lehman, *J. Cell. Physiology*, 85:179, 1975.

Takebe et al., *Mol. Cell. Biol.*, 8:466, 1988.

Takeda, Yonekawa, Tanaka, Okada, Nonaka, Hirokawa, "Left-right asymmetry and kinesin superfamily protein KIF3A: new insights in determination of laterality and mesoderm induction by kif3A$^{-/-}$ mice analysis," *J. Cell. Biol.*, 145:825–836, 1999.

Takemura, Okabe, Umeyama, Kanai, Cowan, Hirokawa, "Increased microtubule stability and alpha tubulin acetylation in cells transfected with microtubule-associated proteins MAP1B, MAP2 or tau," *J. Cell. Sci.*, 103 (Pt 4):953–64, 1992.

Tam et al., *J. Am. Chem. Soc.*, 105:6442, 1983.

Tavernier et al., *Nature*, 301:634, 1983.

Taylor and Kingston, *Mol. Cell. Biol.*, 10:165, 1990a.

Taylor and Kingston, *Mol. Cell. Biol.*, 10:176, 1990b.

Taylor et al., *J. Biol. Chem.*, 264:15160, 1989.

Temin, Retrovirus vectors for gene transfer: Efficient integration into and expression of exogenous DNA in vertebrate cell genome. In: *Gene Transfer*, Kucherlapati R, ed., New York, Plenum Press, pp. 149–188, 1986.

Thiesen et al., *J. Virology*, 62:614, 1988.

Tolnay and Probst, Review: tau protein pathology in Alzheimer's disease and related disorders," *Neuropathol. Appl. Neurobiol.*, 25(3):171–87, 1999.

Tongyu, Border, Freemont, Etkin, "Involvement of the rfp tripartite motif in protein-protein interactions and subcellular distribution," *J. Cell Sci.*, 110:1563–1571, 1997.

Top et al., "Immunization with live types 7 and 4 adenovirus vaccines. II. Antibody response and protective effect against acute respiratory disease due to adenovirus type 7," *J. Infect. Dis.*, 124:155–160, 1971.

Toyama, Forry-Schaudies, Hoffman B, Holtzer H. 1982. Effects of taxol and Colcemid on myofibrillogenesis. *Proc. Nat'l Acad. Sci. USA* 79(21):6556–60.

Treisman, *Cell*, 42:889, 1985.

Tronche et al., *Mol. Biol. Med.*, 7:173, 1990.

Tur-Kaspa et al., "Use of electroporation to introduce biologically active foreign genes into primary rat hepatocytes", *Mol. Cell Biol.*, 6:716–718, 1986.

Tyndall et al., *Nuc. Acids. Res.*, 9:6231, 1981.

Vannice and Levinson, *J. Virology*, 62:1305, 1988.

Varmus et al., *Cell*, 25:23–36, 1981.

Vasseur et al., *Proc. Nat'l Acad. Sci. USA.*, 77:1068, 1980.

Wagner et al., *Proc. Nat'l Acad. Sci. USA* 87(9):3410–3414, 1990.

Wang and Calame, *Cell*, 47:241, 1986.

Wang, Peloquin, Zhai, Bulinski, Borisy, "Removal of MAP4 from microtubules in vivo produces no observable phenotype at the cellular level," *J. Cell Biol.*, 132(3):345–357, 1996.

Weber et al., *Cell*, 36:983, 1984.

Webster, "Neonatal rat cardiomyocytes possess a large population of stable microtubules that is enriched in post-translationally modified subunits," *J. Mol. Cell Cardio.*, 10:2813–2824, 1997.

Wong et al., "Appearance of b-lactamase activity in animal cells upon liposome mediated gene transfer", *Gene*, 10:87–94, 1980.

Wu and Wu, "Evidence for targeted gene delivery to HepG2 hepatoma cells in vitro" *Biochemistry*, 27:887–892, 1988.

Wu and Wu, "Receptor-mediated in vitro gene transfections by a soluble DNA carrier system", *J. Biol. Chem.*, 262: 4429–4432, 1987.

Wu and Wu, *Adv. Drug Delivery Rev.*, 12:159–167, 1993.

Wu et al., *Genomics*, 4:560, 1989.

Yamauchi-Takihara, Sole, Liew, Ing, Liew, "Characterization of human cardiac myosin heavy chain genes," *Proc. Nat'l Acad. Sci. USA*, 86(10):3504–8, 1989.

Yang et al., In vivo and in vitro gene transfer to mammalian somatic cells by particle bombardment. *Proc. Na't. Acad. Sci. USA*, 87:9568–9572, 1990.

Zelenin et al., "High-velocity mechanical DNA transfer of the chloramphenicol acetyltransferase gene into rodent liver, kidney and mammary gland cells in organ explants and in vivo", *FEBS Lett.*, 280:94–96, 1991.

---

What is claimed is:

1. An isolated DNA segment encoding a MURF-3 polypeptide either having:
   (i) the amino acid sequence as set forth in SEQ ID NO:6; or
   (ii) a variant of the amino acid sequence set forth in in SEQ ID NO:6 capable of binding a microtubule wherein the variant is encoded by a nucleic acid sequence that hybridizes to SEQ ID NO:5, from position 299 through position 1327, inclusive, under conditions of 10 mM Tris-HCl (pH 8.3), 50 mM KCl, and 1.5 µm MgCl$_2$ at a temperature of 72° C.

2. The DNA segment of claim 1, wherein the MURF-3 polypeptide has the sequence of SEQ ID NO:6.

3. The DNA segment of claim 2, wherein the MURF-3 DNA segment has the sequence of SEQ ID NO:5.

4. The DNA segment of claim 1, wherein the DNA segment is positioned under the control of a promoter.

5. The DNA segment of claim 4, wherein the promoter is not a native MURF-1, MURF-2 or MURF-3 promoter.

6. The DNA segment of claim 4, further comprising a polyadenylation signal.

7. The DNA segment of claim 4, further comprising an origin of replication.

8. The DNA segment of claim 7, wherein the DNA segment is comprised within a viral vector.

9. The DNA segment of claim 8, wherein the DNA segment is comprised within a non-viral vector.

10. A host cell comprising a DNA segment of claim 1, wherein said DNA segment comprises a promoter heterologous to the murine MURF-3-coding region set forth in in SEQ ID NO:5.

11. The host cell of claim 10, further defined as a prokaryotic host cell.

12. The host cell of claim 10, further defined as a eukaryotic host cell.

13. The host cell of claim 12, wherein the host cell is a secretory cell.

14. The host cell of claim 10, wherein the MURF-3 polypeptide has the sequence of SEQ ID NO:6.

15. A method of producing a MURF-3 polypeptide comprising (i) transforming a host cell with an expression cassette comprising the DNA segment of claim 1 and a promoter active in said host cell and capable of directing the expression of said polypeptide and (ii) culturing the host cell under conditions suitable for the expression of the said polypeptide.

* * * * *

SEQUENCE LISTING

```
<160> NUMBER OF SEQ ID NOS: 6

<210> SEQ ID NO 1
<211> LENGTH: 1431
<212> TYPE: DNA
<213> ORGANISM: Mus musculus
<220> FEATURE:
<221> NAME/KEY: CDS
<222> LOCATION: (199)..(1296)

<400> SEQUENCE: 1
aaggagtgta gacagagtgt ctggaaatag acaggggtga gaggagctgt taggggaagg      60
gacaggactc ttccaagagg gagcaatagc cgggatccca agaatccagt cagcctaaac     120
tgaccgagga agggtgcaca ggcagggggag aaggccaacg acagggccac agcgaggcag    180
gctccagagc gccgcggg atg aac ttc acg gtg ggt ttc aag ccg ctg cta      231
                    Met Asn Phe Thr Val Gly Phe Lys Pro Leu Leu
                     1               5                      10 ggg gat gcg cac aac atg gac aac ttg gag aag cag ctc att tgc ccc      279
Gly Asp Ala His Asn Met Asp Asn Leu Glu Lys Gln Leu Ile Cys Pro
             15                  20                  25 atc tgc ctg gag atg ttc tcc aag ccc gtg gtg atc ttg ccc tgc caa      327
Ile Cys Leu Glu Met Phe Ser Lys Pro Val Val Ile Leu Pro Cys Gln
         30                  35                  40 cac aac ctg tgc cgc aag tgt gcc aac gac gtc ttc cag gcc tct aat      375
His Asn Leu Cys Arg Lys Cys Ala Asn Asp Val Phe Gln Ala Ser Asn
     45                  50                  55 cct ctg tgg caa tcc cgg ggc tcc aca acg gtg tct tca gga gga cgt      423
Pro Leu Trp Gln Ser Arg Gly Ser Thr Thr Val Ser Ser Gly Gly Arg
 60                  65                  70                  75
```

-continued

| | |
|---|---|
| ttc cga tgc cca tct tgt agg cac gag gtt gtc ctg gac agg cat ggt<br>Phe Arg Cys Pro Ser Cys Arg His Glu Val Val Leu Asp Arg His Gly<br>                        80                        85                        90 | 471 |
| gtc tat ggc ctg cag cgg aac ctg cta gtg gag aac atc att gac atc<br>Val Tyr Gly Leu Gln Arg Asn Leu Leu Val Glu Asn Ile Ile Asp Ile<br>                        95                        100                      105 | 519 |
| tac aag cag gag tcc tcc cgg cca ctg cac gcc aag gct gaa cag cac<br>Tyr Lys Gln Glu Ser Ser Arg Pro Leu His Ala Lys Ala Glu Gln His<br>               110                        115                      120 | 567 |
| ctc atg tgt gag gag cac gag gac gag aag atc aac atc tac tgc ctg<br>Leu Met Cys Glu Glu His Glu Asp Glu Lys Ile Asn Ile Tyr Cys Leu<br>125                      130                      135 | 615 |
| agc tgc gag gtg ccc acc tgc tct ctc tgc aag gtt ttc ggc gcc cac<br>Ser Cys Glu Val Pro Thr Cys Ser Leu Cys Lys Val Phe Gly Ala His<br>140                      145                      150                      155 | 663 |
| aag gac tgt gag gtg gcc cct ctg ccc acc att tac aaa cgc cag aag<br>Lys Asp Cys Glu Val Ala Pro Leu Pro Thr Ile Tyr Lys Arg Gln Lys<br>                        160                        165                      170 | 711 |
| agt gag ctg agc gat ggc atc gcg atg ctg gtg gcg ggc aat gac cgt<br>Ser Glu Leu Ser Asp Gly Ile Ala Met Leu Val Ala Gly Asn Asp Arg<br>               175                        180                      185 | 759 |
| gtg cag gca gtg atc acc cag atg gag gag gtg tgc cag acc att gag<br>Val Gln Ala Val Ile Thr Gln Met Glu Glu Val Cys Gln Thr Ile Glu<br>                        190                        195                      200 | 807 |
| gac aac agc cgc aga cag aag caa ctg tta aac cag agg ttc gag acc<br>Asp Asn Ser Arg Arg Gln Lys Gln Leu Leu Asn Gln Arg Phe Glu Thr<br>205                      210                      215 | 855 |
| ctg tgc gcg gtt ttg gag gag cgc aag ggc gaa ctg ctt caa gca ctg<br>Leu Cys Ala Val Leu Glu Glu Arg Lys Gly Glu Leu Leu Gln Ala Leu<br>220                      225                      230                      235 | 903 |
| gcc cgg gag cag gag gag aag ttg cag cgc gtg cgg ggc ctc atc cgc<br>Ala Arg Glu Gln Glu Glu Lys Leu Gln Arg Val Arg Gly Leu Ile Arg<br>                        240                        245                      250 | 951 |
| cag tac gga gac cac ttg gag ggc tcc tca aag ctg gtg gag tcc gcc<br>Gln Tyr Gly Asp His Leu Glu Gly Ser Ser Lys Leu Val Glu Ser Ala<br>               255                        260                      265 | 999 |
| atc cag tcc atg gag gag ccg cag atg gct ctc tac ctc cag cag gca<br>Ile Gln Ser Met Glu Glu Pro Gln Met Ala Leu Tyr Leu Gln Gln Ala<br>                        270                        275                      280 | 1047 |
| aag gag ctg atc aac aag gtc ggg gca atg tcg aag gtg gag ctg gca<br>Lys Glu Leu Ile Asn Lys Val Gly Ala Met Ser Lys Val Glu Leu Ala<br>285                      290                      295 | 1095 |
| gga cgg ccg gag cca ggc tat gag agc atg gag caa ttc tct gtg agc<br>Gly Arg Pro Glu Pro Gly Tyr Glu Ser Met Glu Gln Phe Ser Val Ser<br>300                      305                      310                      315 | 1143 |
| gtg gag cac gtg gcc gaa atg ttg cga acc atc gac ttc cag ccg ggc<br>Val Glu His Val Ala Glu Met Leu Arg Thr Ile Asp Phe Gln Pro Gly<br>               320                        325                      330 | 1191 |
| gcc gct ggg gat gaa gag gat gac gac atg gct ttg gat ggg gag gag<br>Ala Ala Gly Asp Glu Glu Asp Asp Asp Met Ala Leu Asp Gly Glu Glu<br>                        335                        340                      345 | 1239 |
| ggc aat gcg ggg ctg gag gag gag cgg ctg gac gtg cca gaa ggc tca<br>Gly Asn Ala Gly Leu Glu Glu Glu Arg Leu Asp Val Pro Glu Gly Ser<br>350                      355                      360 | 1287 |
| ggc ctg cac tgacccgact ctgatccaga gcgcacaccc gaagcgggag<br>Gly Leu His<br>            365 | 1336 |
| ccaagggatg ctgaggatct gcgcagagac caccgcgcca ccaagctcgg cttcccgccc | 1396 | ccgggaaggt tctcaataaa ggactcaagt gtccc                                        1431

<210> SEQ ID NO 2
<211> LENGTH: 366
<212> TYPE: PRT
<213> ORGANISM: Mus musculus

<400> SEQUENCE: 2

Met Asn Phe Thr Val Gly Phe Lys Pro Leu Leu Gly Asp Ala His Asn
  1               5                  10                  15

Met Asp Asn Leu Glu Lys Gln Leu Ile Cys Pro Ile Cys Leu Glu Met
             20                  25                  30

Phe Ser Lys Pro Val Val Ile Leu Pro Cys Gln His Asn Leu Cys Arg
         35                  40                  45

Lys Cys Ala Asn Asp Val Phe Gln Ala Ser Asn Pro Leu Trp Gln Ser
     50                  55                  60

Arg Gly Ser Thr Thr Val Ser Ser Gly Arg Phe Arg Cys Pro Ser
 65                  70                  75                  80

Cys Arg His Glu Val Val Leu Asp Arg His Gly Val Tyr Gly Leu Gln
                 85                  90                  95

Arg Asn Leu Leu Val Glu Asn Ile Ile Asp Ile Tyr Lys Gln Glu Ser
            100                 105                 110

Ser Arg Pro Leu His Ala Lys Ala Glu Gln His Leu Met Cys Glu Glu
        115                 120                 125

His Glu Asp Glu Lys Ile Asn Ile Tyr Cys Leu Ser Cys Glu Val Pro
    130                 135                 140

Thr Cys Ser Leu Cys Lys Val Phe Gly Ala His Lys Asp Cys Glu Val
145                 150                 155                 160

Ala Pro Leu Pro Thr Ile Tyr Lys Arg Gln Lys Ser Glu Leu Ser Asp
                165                 170                 175

Gly Ile Ala Met Leu Val Ala Gly Asn Asp Arg Val Gln Ala Val Ile
            180                 185                 190

Thr Gln Met Glu Glu Val Cys Gln Thr Ile Glu Asp Asn Ser Arg Arg
        195                 200                 205

Gln Lys Gln Leu Leu Asn Gln Arg Phe Glu Thr Leu Cys Ala Val Leu
    210                 215                 220

Glu Glu Arg Lys Gly Glu Leu Leu Gln Ala Leu Ala Arg Glu Gln Glu
225                 230                 235                 240

Glu Lys Leu Gln Arg Val Arg Gly Leu Ile Arg Gln Tyr Gly Asp His
                245                 250                 255

Leu Glu Gly Ser Ser Lys Leu Val Glu Ser Ala Ile Gln Ser Met Glu
            260                 265                 270

Glu Pro Gln Met Ala Leu Tyr Leu Gln Gln Ala Lys Glu Leu Ile Asn
        275                 280                 285

Lys Val Gly Ala Met Ser Lys Val Glu Leu Ala Gly Arg Pro Glu Pro
    290                 295                 300

Gly Tyr Glu Ser Met Glu Gln Phe Ser Val Ser Val Glu His Val Ala
305                 310                 315                 320

Glu Met Leu Arg Thr Ile Asp Phe Gln Pro Gly Ala Ala Gly Asp Glu
                325                 330                 335

Glu Asp Asp Asp Met Ala Leu Asp Gly Glu Gly Asn Ala Gly Leu
            340                 345                 350

Glu Glu Glu Arg Leu Asp Val Pro Glu Gly Ser Gly Leu His
        355                 360                 365

-continued

```
<210> SEQ ID NO 3
<211> LENGTH: 2590
<212> TYPE: DNA
<213> ORGANISM: Mus musculus
<220> FEATURE:
<221> NAME/KEY: CDS
<222> LOCATION: (80)..(1714)

<400> SEQUENCE: 3
ctcgagattt acccttacag aagctgttcg ggagcacctt tcccttggca gcacactcag      60
ggacagggac ggcaaggaa atg agc act tct ctg aat tac aag tct ttc tcc     112
               Met Ser Thr Ser Leu Asn Tyr Lys Ser Phe Ser
                 1               5                  10 aaa gag cag cag acc atg gat aac ttg gaa aag caa ctg atc tgt ccc     160
Lys Glu Gln Gln Thr Met Asp Asn Leu Glu Lys Gln Leu Ile Cys Pro
              15                  20                  25 atc tgc cta gag atg ttc acg aag cct gtg gtc att ctc cct tgc cag     208
Ile Cys Leu Glu Met Phe Thr Lys Pro Val Val Ile Leu Pro Cys Gln
         30                  35                  40 cac aac ctg tgc agg aaa tgt gcc agt gac atc ttc cag gcc tct aac     256
His Asn Leu Cys Arg Lys Cys Ala Ser Asp Ile Phe Gln Ala Ser Asn
     45                  50                  55 ccg tac tta ccc aca aga gga ggc acc acc gtg gca tca ggg ggc cgc     304
Pro Tyr Leu Pro Thr Arg Gly Gly Thr Thr Val Ala Ser Gly Gly Arg
 60                  65                  70                  75 ttc cgc tgt ccc tcc tgc aga cat gag gtg gtg tta gac aga cat ggg     352
Phe Arg Cys Pro Ser Cys Arg His Glu Val Val Leu Asp Arg His Gly
                 80                  85                  90 gtc tat gga ctg cag agg aac ctg ctc gtg gaa aac att att gat atc     400
Val Tyr Gly Leu Gln Arg Asn Leu Leu Val Glu Asn Ile Ile Asp Ile
             95                 100                 105 tac aag cag gaa tcc acc agg cca gaa aaa aaa ttg gac cag ccc atg     448
Tyr Lys Gln Glu Ser Thr Arg Pro Glu Lys Lys Leu Asp Gln Pro Met
        110                 115                 120 tgt gaa gag cat gaa gag gaa cgc atc aac atc tat tgt ctg aac tgt     496
Cys Glu Glu His Glu Glu Glu Arg Ile Asn Ile Tyr Cys Leu Asn Cys
    125                 130                 135 gaa gtg ccc acc tgt tcc ttg tgc aag gtt ttt ggc gcc cat aag gac     544
Glu Val Pro Thr Cys Ser Leu Cys Lys Val Phe Gly Ala His Lys Asp
140                 145                 150                 155 tgc cag gtg gct ccc ctg act cat gtg ttc cag agg cag aag tca gag     592
Cys Gln Val Ala Pro Leu Thr His Val Phe Gln Arg Gln Lys Ser Glu
                160                 165                 170 ctc agt gat ggt att gct gta ctt gtg gga agc aac gat aga gtc cag     640
Leu Ser Asp Gly Ile Ala Val Leu Val Gly Ser Asn Asp Arg Val Gln
            175                 180                 185 ggt gtg atc agc cag ctg gag gac acc tgt aaa act att gag gag tgc     688
Gly Val Ile Ser Gln Leu Glu Asp Thr Cys Lys Thr Ile Glu Glu Cys
        190                 195                 200 tgc aga aag cag aaa cag gac ctg tgt gag aaa ttt gat cac cta tac     736
Cys Arg Lys Gln Lys Gln Asp Leu Cys Glu Lys Phe Asp His Leu Tyr
    205                 210                 215 ggc atc ctg gag gag agg aag act gaa atg acc caa gcc atc act cga     784
Gly Ile Leu Glu Glu Arg Lys Thr Glu Met Thr Gln Ala Ile Thr Arg
220                 225                 230                 235 aca cag gag gag aaa ctg gaa cat gtc cga act ctt atc agg aag tat     832
Thr Gln Glu Glu Lys Leu Glu His Val Arg Thr Leu Ile Arg Lys Tyr
                240                 245                 250 tcc gat cac ctg gag aac gta tcc aag ttg gtg gag tca gga atc cag     880
Ser Asp His Leu Glu Asn Val Ser Lys Leu Val Glu Ser Gly Ile Gln
```

```
                    255              260              265
ttc atg gat gag ccc gaa atg gca gta ttt ctg cag aat gcc aag acc      928
Phe Met Asp Glu Pro Glu Met Ala Val Phe Leu Gln Asn Ala Lys Thr
        270              275              280 ctg ttg caa aag atc gtg gaa gca tca aag gcg ttt cag atg gag aaa      976
Leu Leu Gln Lys Ile Val Glu Ala Ser Lys Ala Phe Gln Met Glu Lys
285              290              295 cta gaa caa ggt tat gag atc atg agc aac ttc act gtc aat ctc aat     1024
Leu Glu Gln Gly Tyr Glu Ile Met Ser Asn Phe Thr Val Asn Leu Asn
300              305              310              315 aga gaa gaa aaa att atc cgt gaa att gac ttt tct aga gaa gag gaa     1072
Arg Glu Glu Lys Ile Ile Arg Glu Ile Asp Phe Ser Arg Glu Glu Glu
            320              325              330 gag gaa gaa gat gca gga gaa ata gat gaa gaa gga gaa gga gag gat     1120
Glu Glu Glu Asp Ala Gly Glu Ile Asp Glu Glu Gly Glu Gly Glu Asp
        335              340              345 gca gta gaa gta gaa gag gca gaa aat gtt caa ata gca tct tca ggg     1168
Ala Val Glu Val Glu Glu Ala Glu Asn Val Gln Ile Ala Ser Ser Gly
    350              355              360 gaa gag gag agt ctg gag aaa gct gca gag ccc tct cag ctt ccc gca     1216
Glu Glu Glu Ser Leu Glu Lys Ala Ala Glu Pro Ser Gln Leu Pro Ala
365              370              375 gag ctt cag gtc gcc cca gag cca cta cct gct tcc tct cca gaa ccg     1264
Glu Leu Gln Val Ala Pro Glu Pro Leu Pro Ala Ser Ser Pro Glu Pro
380              385              390              395 ttt tca tcc atg cca cct gct gca gat gtc ctg gtg aca cag ggg gag     1312
Phe Ser Ser Met Pro Pro Ala Ala Asp Val Leu Val Thr Gln Gly Glu
            400              405              410 gtg gtg ccc att ggc tct cag cag acc aca cag tct gaa act tca ggc     1360
Val Val Pro Ile Gly Ser Gln Gln Thr Thr Gln Ser Glu Thr Ser Gly
        415              420              425 cct tca gca gcg gaa act gcg gat ccc ttg ttt tac cct agt tgg tat     1408
Pro Ser Ala Ala Glu Thr Ala Asp Pro Leu Phe Tyr Pro Ser Trp Tyr
    430              435              440 aaa ggc caa agc cgg aaa acc agc tcc aac cca cct tgc act cat ggg     1456
Lys Gly Gln Ser Arg Lys Thr Ser Ser Asn Pro Pro Cys Thr His Gly
445              450              455 agt gaa ggt ctg ggt caa ata ggg cct ctg ggc att gag gat tcc agt     1504
Ser Glu Gly Leu Gly Gln Ile Gly Pro Leu Gly Ile Glu Asp Ser Ser
460              465              470              475 gtg cag tcc gca gaa gtg gca gaa gcc gca acc aat gag cag gca gca     1552
Val Gln Ser Ala Glu Val Ala Glu Ala Ala Thr Asn Glu Gln Ala Ala
            480              485              490 gtg agt ggt aag gag tct agt tca act gca gct acc tct cag att gga     1600
Val Ser Gly Lys Glu Ser Ser Ser Thr Ala Ala Thr Ser Gln Ile Gly
        495              500              505 ttt gag gcc cct tct ccc cag gga cag tct gca gcc ttg ggg agt ggg     1648
Phe Glu Ala Pro Ser Pro Gln Gly Gln Ser Ala Ala Leu Gly Ser Gly
    510              515              520 ggt ggg gtg atc ctg agc cag ctc gcc acg tct tct cct tct cct ggt     1696
Gly Gly Val Ile Leu Ser Gln Leu Ala Thr Ser Ser Pro Ser Pro Gly
525              530              535 ttg aat tcc cta aat gaa taatatttat tctcgttgct gccccctgtc            1744
Leu Asn Ser Leu Asn Glu
540              545 tgcctggctg aaaagcacat aggcagcagg aaacaggtgg aaattcacca cgattcatat   1804 gaagggacc tctggacagg atttctgaaa gcaaaacaaa acaatacaac accaccaccc    1864
tttaattcca gatgacttat ctcactcatt gagaaaatga ttatgctcag aacaaaatta  1924
```

```
cagaaaatac tcttctgaag aaacttgatc ttctgcaaat ctttcatttg tgtgagaaac   1984
cttctgaagg ttgtgtaggt gtggtgcatg cctgtgtatc agccataagt gccaagtggt   2044
aacaaagtgg cagaacactc tcccagcctc cctcaggctt ctggttattt taggacgctt   2104
gtgccttttg cttttctcct tagcattgca ggtggtaggt gatgttcagt gtcagttcca   2164
aactgaccga tttatcaaaa tatggagatt ggtcactgac caaagctatg tagggcactg   2224
tagaggttcc tttccctatg gatgccatgg gtgcgcagac aggactttcc tttacatgtg   2284
gccacacgtc catagtccag aaggccaaaa atctagggca actcttttga cattttcta    2344 accttattta catatctcat aatcatatcc atgtattagg cattttaatt gaatttcaaa   2404
gaggagctgt ctactttctt aagtgtcctg ccatagcagc aatctgataa tctgtggagc   2464
aactgcatgg atttaagtat acacacaatt ctcccctgt gtgccttctc tctctctctc    2524 tctcccctc tctccctctg tctcttctct cccctctgt ctctccctcc tttcctttct     2584
tcctcc                                                               2590
```

<210> SEQ ID NO 4
<211> LENGTH: 545
<212> TYPE: PRT
<213> ORGANISM: Mus musculus

<400> SEQUENCE: 4

```
Met Ser Thr Ser Leu Asn Tyr Lys Ser Phe Ser Lys Glu Gln Gln Thr
  1               5                  10                  15

Met Asp Asn Leu Glu Lys Gln Leu Ile Cys Pro Ile Cys Leu Glu Met
             20                  25                  30

Phe Thr Lys Pro Val Val Ile Leu Pro Cys Gln His Asn Leu Cys Arg
         35                  40                  45

Lys Cys Ala Ser Asp Ile Phe Gln Ala Ser Asn Pro Tyr Leu Pro Thr
     50                  55                  60

Arg Gly Gly Thr Thr Val Ala Ser Gly Gly Arg Phe Arg Cys Pro Ser
 65                  70                  75                  80

Cys Arg His Glu Val Val Leu Asp Arg His Gly Val Tyr Gly Leu Gln
                 85                  90                  95

Arg Asn Leu Leu Val Glu Asn Ile Ile Asp Ile Tyr Lys Gln Glu Ser
            100                 105                 110

Thr Arg Pro Glu Lys Lys Leu Asp Gln Pro Met Cys Glu Glu His Glu
        115                 120                 125

Glu Glu Arg Ile Asn Ile Tyr Cys Leu Asn Cys Glu Val Pro Thr Cys
    130                 135                 140

Ser Leu Cys Lys Val Phe Gly Ala His Lys Asp Cys Gln Val Ala Pro
145                 150                 155                 160

Leu Thr His Val Phe Gln Arg Gln Lys Ser Glu Leu Ser Asp Gly Ile
                165                 170                 175

Ala Val Leu Val Gly Ser Asn Asp Arg Val Gln Gly Val Ile Ser Gln
            180                 185                 190

Leu Glu Asp Thr Cys Lys Thr Ile Glu Glu Cys Cys Arg Lys Gln Lys
        195                 200                 205

Gln Asp Leu Cys Glu Lys Phe Asp His Leu Tyr Gly Ile Leu Glu Glu
    210                 215                 220

Arg Lys Thr Glu Met Thr Gln Ala Ile Thr Arg Thr Gln Glu Glu Lys
225                 230                 235                 240

Leu Glu His Val Arg Thr Leu Ile Arg Lys Tyr Ser Asp His Leu Glu
```

-continued

```
                245                 250                 255
Asn Val Ser Lys Leu Val Glu Ser Gly Ile Gln Phe Met Asp Glu Pro
                260                 265                 270
Glu Met Ala Val Phe Leu Gln Asn Ala Lys Thr Leu Leu Gln Lys Ile
            275                 280                 285
Val Glu Ala Ser Lys Ala Phe Gln Met Glu Lys Leu Glu Gln Gly Tyr
        290                 295                 300
Glu Ile Met Ser Asn Phe Thr Val Asn Leu Asn Arg Glu Glu Lys Ile
305                 310                 315                 320
Ile Arg Glu Ile Asp Phe Ser Arg Glu Glu Glu Glu Asp Ala
                325                 330                 335
Gly Glu Ile Asp Glu Glu Gly Glu Asp Ala Val Glu Val Glu
                340                 345                 350
Glu Ala Glu Asn Val Gln Ile Ala Ser Ser Gly Glu Glu Ser Leu
            355                 360                 365
Glu Lys Ala Ala Glu Pro Ser Gln Leu Pro Ala Glu Leu Gln Val Ala
        370                 375                 380
Pro Glu Pro Leu Pro Ala Ser Ser Pro Glu Pro Phe Ser Ser Met Pro
385                 390                 395                 400
Pro Ala Ala Asp Val Leu Val Thr Gln Gly Glu Val Val Pro Ile Gly
                405                 410                 415
Ser Gln Gln Thr Thr Gln Ser Glu Thr Ser Gly Pro Ser Ala Ala Glu
            420                 425                 430
Thr Ala Asp Pro Leu Phe Tyr Pro Ser Trp Tyr Lys Gly Gln Ser Arg
        435                 440                 445
Lys Thr Ser Ser Asn Pro Pro Cys Thr His Gly Ser Glu Gly Leu Gly
    450                 455                 460
Gln Ile Gly Pro Leu Gly Ile Glu Asp Ser Ser Val Gln Ser Ala Glu
465                 470                 475                 480
Val Ala Glu Ala Ala Thr Asn Glu Gln Ala Ala Val Ser Gly Lys Glu
                485                 490                 495
Ser Ser Ser Thr Ala Ala Thr Ser Gln Ile Gly Phe Glu Ala Pro Ser
            500                 505                 510
Pro Gln Gly Gln Ser Ala Ala Leu Gly Ser Gly Gly Val Ile Leu
        515                 520                 525
Ser Gln Leu Ala Thr Ser Ser Pro Ser Pro Gly Leu Asn Ser Leu Asn
    530                 535                 540
Glu
545
```

<210> SEQ ID NO 5
<211> LENGTH: 1597
<212> TYPE: DNA
<213> ORGANISM: Mus musculus
<220> FEATURE:
<221> NAME/KEY: CDS
<222> LOCATION: (299)..(1327)

<400> SEQUENCE: 5

```
ctcgagattt acccttacag aagctgttcg ggagcacctt tcccttggca gcacactcag      60
ggacagggac ggcaaggaaa tgagcacttc tctgaattac aagtcttct  ccaaagagca     120
gcagaccatg gataacttgg aaaagcaact gatctgtccc atctgcctag agatgttcac     180
gaagcctgtg gtcattctcc cttgccagca caacctgtgc aggaaatgtg cgggcccccc     240
ttggagacaa agacttggtg tgacgcaggt gggcaagaca gtcgcatttc aaagcaat      298
```

```
atg gat tat aaa tct agc ctg att cct gat gga aac gct atg gag aac      346
Met Asp Tyr Lys Ser Ser Leu Ile Pro Asp Gly Asn Ala Met Glu Asn
 1               5                  10                  15 ctg gag aag cag ctg atc tgc ccc atc tgc ctg gag atg ttt acc aag      394
Leu Glu Lys Gln Leu Ile Cys Pro Ile Cys Leu Glu Met Phe Thr Lys
                 20                  25                  30 cct gtg gtc atc ctg ccc tgc caa cac aac ctc tgc cgg aag tgt gcc      442
Pro Val Val Ile Leu Pro Cys Gln His Asn Leu Cys Arg Lys Cys Ala
             35                  40                  45 aac gac atc ttc cag gct gcg aat ccc tac tgg acc aac cgc ggt ggc      490
Asn Asp Ile Phe Gln Ala Ala Asn Pro Tyr Trp Thr Asn Arg Gly Gly
         50                  55                  60 tca gtg tcc atg tct gga ggt cgt ttc cgt tgc ccc tcg tgc cgc cat      538
Ser Val Ser Met Ser Gly Gly Arg Phe Arg Cys Pro Ser Cys Arg His
 65                  70                  75                  80 gaa gtg atc atg gac cgg cac ggg gtg tac ggc ctg cag agg aac ctg      586
Glu Val Ile Met Asp Arg His Gly Val Tyr Gly Leu Gln Arg Asn Leu
                 85                  90                  95 ctg gtg gaa aac atc att gac atc tac aag cag gag tgc tcc agt cgg      634
Leu Val Glu Asn Ile Ile Asp Ile Tyr Lys Gln Glu Cys Ser Ser Arg
             100                 105                 110 ccc ctg cag aaa ggc agc cac ccg atg tgc aag gaa cac gaa gac gag      682
Pro Leu Gln Lys Gly Ser His Pro Met Cys Lys Glu His Glu Asp Glu
         115                 120                 125 aag atc aac atc tac tgt ctc acg tgt gag gtg cct act tgc tcc ttg      730
Lys Ile Asn Ile Tyr Cys Leu Thr Cys Glu Val Pro Thr Cys Ser Leu
     130                 135                 140 tgc aag gtg ttt ggg gct cac cag gcc tgt gag gtt gcc cct ttg caa      778
Cys Lys Val Phe Gly Ala His Gln Ala Cys Glu Val Ala Pro Leu Gln
145                 150                 155                 160 agc atc ttc caa gga cag aag act gag ctg agt aac tgc atc tcc atg      826
Ser Ile Phe Gln Gly Gln Lys Thr Glu Leu Ser Asn Cys Ile Ser Met
                 165                 170                 175 ctg gtg gcg ggg aac gac cga gtg cag acg atc atc tct cag ctg gag      874
Leu Val Ala Gly Asn Asp Arg Val Gln Thr Ile Ile Ser Gln Leu Glu
             180                 185                 190 gac tcg tgc aga gtg acc aag gag aat agc cac cag gtg aag gag gag      922
Asp Ser Cys Arg Val Thr Lys Glu Asn Ser His Gln Val Lys Glu Glu
         195                 200                 205 ctg agt cag aag ttt gac acc ctc tac gcc atc ctg gat gag aag aag      970
Leu Ser Gln Lys Phe Asp Thr Leu Tyr Ala Ile Leu Asp Glu Lys Lys
     210                 215                 220 agc gag ctg ctg cag cgg atc acg cag gag cag gag gag aag ctg ggc     1018
Ser Glu Leu Leu Gln Arg Ile Thr Gln Glu Gln Glu Glu Lys Leu Gly
225                 230                 235                 240 ttc atc gag gct ctg atc ctc cag tac agg gag cag ctg gaa aag tcc     1066
Phe Ile Glu Ala Leu Ile Leu Gln Tyr Arg Glu Gln Leu Glu Lys Ser
                 245                 250                 255 acc aag ctt gtg gag acc gcc atc cag tcc ctg gat gag ccc gga ggg     1114
Thr Lys Leu Val Glu Thr Ala Ile Gln Ser Leu Asp Glu Pro Gly Gly
             260                 265                 270 gct acc ttc ctc tca agt gcc aag cag ctc atc aag agc att gta gaa     1162
Ala Thr Phe Leu Ser Ser Ala Lys Gln Leu Ile Lys Ser Ile Val Glu
         275                 280                 285 gcc tcc aag ggc tgc cag ctg ggg aag aca gag caa ggc ttt gag aac     1210
Ala Ser Lys Gly Cys Gln Leu Gly Lys Thr Glu Gln Gly Phe Glu Asn
     290                 295                 300 atg gac tac ttt act ctg gac tta gaa cac ata gca gag gcc ttg agg     1258
Met Asp Tyr Phe Thr Leu Asp Leu Glu His Ile Ala Glu Ala Leu Arg
```

```
                305                 310                 315                 320
gcc att gac ttt ggg aca ggt aaa gga tgt gat gtt aca tgt ttg acc         1306
Ala Ile Asp Phe Gly Thr Gly Lys Gly Cys Asp Val Thr Cys Leu Thr
                    325                 330                 335 ttt gaa agg cag cgt tcc tct tgagttctga ggggaactgt taaaaaagtc            1357
Phe Glu Arg Gln Arg Ser Ser
                340 aaatttacac agccagtgtt gacaggtctc tctatggagc cctgactgtc ttagtagtgt        1417 ctaagtagac caagctggtc tggaacacat agagatctat cttgcccatc tctgcttctt        1477 gagggatgag ataaaaggca tgtgcccacc atgcctggct ccacagacaa ctttgtgatg        1537 gatccagggt ctggcacagt gcctggtaca taattgtttc gaaataaatt atctcgtgcc        1597

<210> SEQ ID NO 6
<211> LENGTH: 343
<212> TYPE: PRT
<213> ORGANISM: Mus musculus

<400> SEQUENCE: 6

Met Asp Tyr Lys Ser Ser Leu Ile Pro Asp Gly Asn Ala Met Glu Asn
  1               5                  10                  15

Leu Glu Lys Gln Leu Ile Cys Pro Ile Cys Leu Glu Met Phe Thr Lys
                 20                  25                  30

Pro Val Ile Leu Pro Cys Gln His Asn Leu Cys Arg Lys Cys Ala
             35                  40                  45

Asn Asp Ile Phe Gln Ala Ala Asn Pro Tyr Trp Thr Asn Arg Gly Gly
         50                  55                  60

Ser Val Ser Met Ser Gly Gly Arg Phe Arg Cys Pro Ser Cys Arg His
 65                  70                  75                  80

Glu Val Ile Met Asp Arg His Gly Val Tyr Gly Leu Gln Arg Asn Leu
                 85                  90                  95

Leu Val Glu Asn Ile Ile Asp Ile Tyr Lys Gln Glu Cys Ser Ser Arg
            100                 105                 110

Pro Leu Gln Lys Gly Ser His Pro Met Cys Lys Glu His Glu Asp Glu
            115                 120                 125

Lys Ile Asn Ile Tyr Cys Leu Thr Cys Glu Val Pro Thr Cys Ser Leu
130                 135                 140

Cys Lys Val Phe Gly Ala His Gln Ala Cys Glu Val Ala Pro Leu Gln
145                 150                 155                 160

Ser Ile Phe Gln Gly Gln Lys Thr Glu Leu Ser Asn Cys Ile Ser Met
                165                 170                 175

Leu Val Ala Gly Asn Asp Arg Val Gln Thr Ile Ile Ser Gln Leu Glu
            180                 185                 190

Asp Ser Cys Arg Val Thr Lys Glu Asn Ser His Gln Val Lys Glu Glu
            195                 200                 205

Leu Ser Gln Lys Phe Asp Thr Leu Tyr Ala Ile Leu Asp Glu Lys Lys
        210                 215                 220

Ser Glu Leu Leu Gln Arg Ile Thr Gln Glu Gln Glu Lys Leu Gly
225                 230                 235                 240

Phe Ile Glu Ala Leu Ile Leu Gln Tyr Arg Glu Gln Leu Glu Lys Ser
                245                 250                 255

Thr Lys Leu Val Glu Thr Ala Ile Gln Ser Leu Asp Glu Pro Gly Gly
            260                 265                 270

Ala Thr Phe Leu Ser Ser Ala Lys Gln Leu Ile Lys Ser Ile Val Glu
        275                 280                 285
```

```
Ala Ser Lys Gly Cys Gln Leu Gly Lys Thr Glu Gln Gly Phe Glu Asn
    290                 295                 300

Met Asp Tyr Phe Thr Leu Asp Leu Glu His Ile Ala Glu Ala Leu Arg
305             310             315                 320

Ala Ile Asp Phe Gly Thr Gly Lys Gly Cys Asp Val Thr Cys Leu Thr
                325             330             335

Phe Glu Arg Gln Arg Ser Ser
            340
```